US008076077B2

(12) United States Patent
Cheung et al.

(10) Patent No.: US 8,076,077 B2
(45) Date of Patent: Dec. 13, 2011

(54) COMPOSITIONS AND METHODS FOR PROGNOSIS AND THERAPY OF LIVER CANCER

(75) Inventors: Siu Tim Cheung, Hong Kong (CN); Sheung Tat Fan, Hong Kong (CN)

(73) Assignee: Versitech Limited, Hong Kong (CN)

( * ) Notice: Subject to any disclaimer, the term of this patent is extended or adjusted under 35 U.S.C. 154(b) by 482 days.

(21) Appl. No.: 12/255,092

(22) Filed: Oct. 21, 2008

(65) Prior Publication Data

US 2009/0325160 A1 Dec. 31, 2009

Related U.S. Application Data

(62) Division of application No. 10/917,195, filed on Aug. 12, 2004, now abandoned.

(60) Provisional application No. 60/494,981, filed on Aug. 13, 2003, provisional application No. 60/500,844, filed on Sep. 4, 2003.

(51) Int. Cl.
*C12Q 1/68* (2006.01)
(52) U.S. Cl. .................. 435/6.1; 435/6.11; 435/6.14
(58) Field of Classification Search .................. None
See application file for complete search history.

(56) References Cited

U.S. PATENT DOCUMENTS

2003/0165854 A1* 9/2003 Cunningham et al. ............ 435/6

OTHER PUBLICATIONS

Beer, D.G. et al., "Gene-Expression Profiles Predict Survival of Patients with Lung Adenocarcinoma," Nature Medicine, 2002, 816-824, vol. 8, No. 8.
Van'T Veer, L.J. et al., "Gene Expression Profiling Predicts Clinical Outcome of Breast Cancer," Nature, 2002, 530-536, vol. 415.
Kawai, H.F. et al., "α-Fetoprotein-Producing Hepatoma Cell Lines Share Common Expression Profiles of Genes . . . ," Hepatology, 2001,676-691, vol. 33.
Sobin, L.H. and Wittekind, C., TNM Classification of Malignant Tumors, 1997, 5th ed., Wiley-Liss, New York, USA.
SAS Institute, SAS Macro Language: Reference, First Edition, 1997, 1st ed.
Fan, S-T. et al., "Hepatectomy for Hepatocellular Carcinoma: Toward Zero Hospital Deaths," Annals of Surgery, 1999,322-330, vol. 229, No. 3.
Pisani, P. et al., "Estimates of the Worldwide Mortality from 25 Cancers in 1990," Int. J. Cancer, 1999, 18-29, vol. 83.
El-Serag, H. B. and Mason, A.C., "Rising Incidence of Hepatocellular Carcinoma in the United States," N. Engl. J. Med., 1999, 745-750, vol. 340.
Taylor-Robinson, S. et al., "Increase in Primary Liver Cancer in the UK, 1979-94," The Lancet, 1997, 1142-1143, vol. 350.
Okuda, K. et al., "Changing Incidence of Hepatocellular Carcinoma in Japan," Cancer Research, 1987, 4967-4972, vol. 47.

Tang, Z., "Hepatocellular Carcinoma," Journal of Gastroenterology and Hepatology—Quadrennial Review, 2000, G1-G7, vol. 15.
Ng, I. et al., "Prognostic Significance of Pathologic Features of Hepatocellular Carcinoma . . . ," Cancer, 1995, 2443-2448, vol. 76, No. 12.
Ng, I. et al., "Clinicopathologic and Prognostic Significance of the Histologic Activity of Noncancerous Liver Tissue in Hepatis B . . . " Anatomic Pathology, 2002, 411-418.
Poon, R. et al., "Different Risk Factors and Prognosis for Early and Late Intrahepatic Recurrence . . . ," Cancer, 2000, 500-507, vol. 89.
Poon, R. et al., "Improving Survival Results After Resection of Hepatocellular Carcinoma: A Prospective Study . . . " Annals of Surgery, 2001, 63-70, vol. 234, No. 1.
Poon, R. et al., "Clinicopathologic Features of Long-Term Survivors and Disease-Free Survivors . . . ," J. Clin. Oncol., 2001, 3037-3044, vol. 19, No. 12.
Vauthey, J. et al., "Simplified Staging for Hepatocellular Carcinoma," Journal of Clinical Oncology, 2002,1527-1536, vol. 20, No. 6.
Villa, E. et al., "Estrogen Receptor Classification for Hepatocellular Carcinoma: Comparison with Clinical Staging Systems," J. Clin. Oncol., 2003, 441-446, vol. 21, No. 3.
Yeatman, T., "The Future of Cancer Management: Translating the Genome, Transcriptome, and Proteome," Annals of Surgical Oncology, 2003, 7-14, vol. 10, No. 1.
Dhanasekaran, S. et al., "Delineation of Prognostic Biomarkers in Prostate Cancer," Nature, 2001, 822-825, vol. 412.
Garber, M. et al., "Diversity of Gene Expression in Adenocarcinoma of the Lung," PNAS, 2001,13784-13789, vol. 98, No. 24.
Pomeroy, S. et al., "Prediction of Central Nervous System Embryonal Tumour Outcome Based on Gene Expression," Nature, 2002,436-442, vol. 415.
Singh, D. et al., "Gene Expression Correlates of Clinical Prostate Cancer Behavior," Cancer Cell, 2002, 203-209, vol. 1.

(Continued)

*Primary Examiner* — Michael Burkhart
(74) *Attorney, Agent, or Firm* — Saliwanchik, Lloyd & Eisenschenk

(57) ABSTRACT

This invention provides a composition comprising the following polynucleotide probes: IL7R (AA485865) (SEQ ID NO:7), NDRGI (AA486403) (SEQ ID NO:8), EST1 (H50345) (SEQ ID NO:9), TRPC1 (AA017132) (SEQ ID NO:10), GFRA1 (AA512935) (SEQ ID NO:11), EST2 (AA454543) (SEQ ID NO:12), CLDN10 (R54559) (SEQ ID NO:13), DNALI1 (R93087) (SEQ ID NO:14), RBP5 (AA453198) (SEQ ID NO:15), EST3 (AA621761) (SEQ ID NO:16), EST4 (N63706) (SEQ ID NO:17), PCOLCE (AA670200) (SEQ ID NO:18), TDO2 (T72398) (SEQ ID NO:19), EST5 (T47454) (SEQ ID NO:20), HIST1H2BD (N33927) (SEQ ID NO:21), PXMP2 (N70714) (SEQ ID NO:22), ACAS2 (AA455146) (SEQ ID NO:23), ANAPC7 (T68445) (SEQ ID NO:24), EST6 (AA576580) (SEQ ID NO:25), RBP5 (N92148) (SEQ ID NO:26), ANXAI (H63077) (SEQ ID NO:27), CKB (AA894557) (SEQ ID NO:28), ITGBL1 (N52533) (SEQ ID NO:29), KPNA2 (AA676460) (SEQ ID NO:30), EST7 (W90740) (SEQ ID NO:31) and MEG3 (W85841) (SEQ ID NO:32). This invention further provides methods for determining the likelihood of recurrence of hepatocellular carcinoma (HCC) in a subject afflicted with HCC, for determining the likelihood of death of a subject afflicted with HCC or for determining whether to administer adjuvant therapy.

1 Claim, 10 Drawing Sheets

OTHER PUBLICATIONS

Sorlie, T. et al., "Gene Expression Patterns of Breast Carcinomas Distinguish Tumor Subclasses with Clinical Implications," PNAS, 2001,10869-10874, vol. 98, No. 19.

Van De Vijver, M. et al., "A Gene-Expression Signature as a Predictor of Survival in Breast Cancer," New Engl. J. Med., 2002, 1999-2009, vol. 347, No. 25.

Lee, J-S. and Thorgeirsson, S., "Functional and Genomic Implications of Global Gene Expression Profiles . . . ," Hepatology, 2002, 1134-1143, vol. 35.

Okabe, H. et al., "Genome-wide Analysis of Gene Expression in Human Hepatocellular Carcinomas Using cDNA Microarray . . . ," Cancer Research, 2001, 2129-2137, vol. 61.

Shirota, Y. et al., "Identification of Differentially Expressed Genes in Hepatocellular Carcinoma With cDNA Microarrays," Hepatology, 2001,832-840, vol. 33.

Xu, X. et al., "Insight into Hepatocellular Carcinogenesis at Transcriptome Level by Comparing Gene Expression Profiles . . . ," PNAS, 2001, 15089-15094, vol. 98, No. 26.

Chen, X., et al., "Gene Expression Patterns in Human Liver Cancers," Molecular Biology of the Cell, 2002,1929-1939, vol. 13.

Cheung, S. et al., "Identify Metastasis-associated Genes in Hepatocellular Carcinoma through Clonality Delineation . . . ," Cancer Research, 2002, 4711-4721, vol. 62.

Iizuka, N. et al., "Oligonucleotide Microarray for Prediction of Early Intrahepatic Recurrence of Hepatocellular Carcinoma . . . ," The Lancet, 2003, 923-929, vol. 361.

Youden, W.J., "Index for Rating Diagnostic Tests," Cancer, 1950,32-35.

Edmondson, H. and Steiner, P., "Primary Carcinoma of the Liver: A Study of 100 Cases among 48,900 Necropsies," Cancer, 1954,462-503, vol. 7.

Gonzalez-Mariscal, L. et al., "Tight Junction Proteins," Progress in Biophysics & Molecular Biology, 2003, 1-44, vol. 81.

Kastury, K. et al., "Complementary Deoxyribonucleic Acid Cloning and Characterization of . . . ," Journal of Clinical Endocrinology and Metabolism, 1997, 3047-3053, vol. 82, No. 9.

Schwartz, J. et al., "Neoadjuvant and Adjuvant Therapy for Resectable Hepatocellular Carcinoma: Review of the Randomised Clinical Trials," The Lancet, 2002, 593-603, vol. 3.

Poon, R. et al., "Risk Factors, Prevention, and Management of Postoperative Recurrence After Resection of Hepatocellular Carcinoma," Annals of Surgery, 2000, 10-24, vol. 232.

Muto, Y. et al., "Prevention of Second Primary Tumors by an Acyclic Retinoid, Polyprenoic Acid, in Patients . . . ," New Engl. J. Med., 1996, 1561-1567, vol. 334, No. 24.

Marill, J. et al., "Retinoic Acid Metabolism and Mechanism of Action: A Review," Current Drug Metabolism, 2003, 1-10, vol. 4.

DeRisi, J. et al., "Use of a cDNA Microarray to Analyse Gene Expression Patterns in Human Cancer," Nature Genetics, 1996, 457-460, vol. 14.

Perou, C. et al., "Molecular Portraits of Human Breast Tumours," Nature, 2000,747-752, vol. 406.

Sherlock, G. et al., "The Stanford Microarray Database," Nucleic Acids Research, 2001, 152-155, vol. 29, No. 1.

Eisen, M. et al., "Cluster Analysis and Display of Genome-wide Expression Patterns," Proc. Natl. Acad. Sci. USA, 1998, 14863-14868, vol. 95.

Bustin, S., "Absolute Quantification of mRNA Using Real-time Reverse Transcription Polymerase Chain Reaction Assays," J. Mol. Endocrin., 2000, 169-193, vol. 25.

Brazma, A. et al., "Minimum Information about a Microarray Experiment (MIAME)—Toward Standards for Microarray Data," Nature Genetics, 2001, 365-371. vol. 29.

Ng, I. et al., "Pathologic Features and Patient Survival in Hepatocellular Carcinoma in Relation to Age," Journal of Surgical Oncology, 1996, 134-137, vol. 61.

Ng, I. et al., "Tumor Encapsulation in Hepatocellular Carcinoma: A Pathologic Study of 189 Cases," Cancer, 1992, 45-49, vol. 70.

Fan, S. et al., "Methods and Related Drawbacks in the Estimation of Surgical Risks in Cirrhotic Patients Undergoing Hepatectomy," Hepato-Gastroenterology, 2002, 17-20, vol. 49.

Simon, R. et al., "Pitfalls in the Use of DNA Microarray Data for Diagnostic and Prognostic Classification," Journal of the National Cancer Institute, 2003, 14-18.

Sugita, M. et al., "Combined Use of Oligonucleotide and Tissue Microarrays Identifies Cancer/Testis Antigens . . . ," Cancer Research, 2002, 3971-3979, vol. 62.

Poon, R. and Fan, S., "Evaluation of the New AJCC/UICC Staging System for Hepatocellular Carcinoma . . . ," Surg. Oncol. Clin; N. Am., 2003, 35-50, vol. 12.

Neo, S. et al., "Identification of Discriminators of Hepatoma by Gene Expression Profiling Using a Minimal Dataset Approach," Hepatology, 2004, 944-953, vol. 39.

Amasheh, S. et al., "Claudin-2 Expression Induces Cation-Selective Channels in Tight Junctions of Epithelial Cells," Journal of Cell Science, 2002, 4969-4976, vol. 115.

Tiwari-Woodruff, S. et al., "OSP/Claudin-11 Forms a Complex with a Novel Member of the Tetraspanin Super Family . . . ," The Journal of Cell Biology, 2001, 295-305, vol. 153.

Nichols, L. et al., "Claudin 4 Protein Expression in Primary and Metastatic Pancreatic Cancer," American Journal of Clinical Pathology, 2004, 226-230, vol. 121.

Michl, P. et al., "Claudin-4: A New Target for Pancreatic Cancer Treatment Using Clostridium Perfringens Enterotoxin," Gastroenterology, 2001, 678-684, vol. 121.

Miwa, N. et al., "Involvement of Claudin-1 in the β-Catenin/Tcf Signaling Pathway and its Frequent Upregulation . . . , " Oncology Research, 2001, 469-476, vol. 12.

Rangel, L. et al., "Tight Junction Proteins Claudin-3 and Claudin-4 are Frequently Overexpressed in Ovarian Cancer . . . ," Clinical Cancer Research, 2003, 2567-2575, vol. 9.

Michl, P. et al., "Claudin-4 Expression Decreases Invasiveness and Metastatic Potential of Pancreatic Cancer," Cancer Research, 2003,6265-6271, vol. 63.

Al Moustafa, A. et al., "Identification of Genes Associated with Head and Neck Carcinogenesis by cDNA Microarray Comparison . . . ," Oncogene, 2002, 2634-2640, vol. 21.

Kominsky, S. et al., "Loss of the Tight Junction Protein Claudin-7 Correlates with Histological Grade in Both Ductal Carcinoma . . . ," Oncogene, 2003, 2021-2033, vol. 22.

Kramer, F. et al., "Genomic Organization of Claudin-1 and its Assessment in Hereditary and Sporadic Breast Cancer," Hum. Genet., 2000, 249-256, vol. 107.

Furata, T. et al., "Clinicopathologic Features of Hepatocellular Carcinoma in Young Patients," Cancer, 1990, 2395-2398, vol. 66.

Vauthey. J. et al., "Factors Affecting Long-Term Outcome After Hepatic Resection for Hepatocellular Carcinoma," The American Journal of Surgery, 1995, 28-34, vol. 169.

Bruix, J. et al. , "Focus on Hepatocellular Carcinoma," Cancer Cell, 2004, 215-219, vol. 5.

Fong, Y. et al., "An Analysis of 412 Cases of Hepatocellular Carcinoma at a Western Center," Annals of Surgery, 1999, 790-800, vol. 229, No. 6.

Neuhaus, P. et al., "Hepatoma of the Liver—Resection or Transplantation?" Langenbeck's Arch. Surg., 2000,171-178, vol. 385.

Nagasue, N. et al., "Liver Resection for Hepatocellular Carcinoma: Results of 229 Consecutive Patients During 11 Years," Annals of Surgery, 1993, 375-384, vol. 217, No. 4.

Lise, M. et al., "Prognostic Factors Affecting Long Term Outcome after Liver Resection for Hepatocellular Carcinoma," Cancer, 1998,1028-1036, vol. 82.

Pepe, M. et al., "Limitations of the Odds Ratio in Gauging the Performance of a Diagnostic . . . ," Amer. J. Epiderm., 2004, 882-890, vol. 159, No. 9.

Collins, F. et al., "A Vision for the Future of Genomics Research: A Blueprint for the Genomic Era," Nature, 2003, 835-847, vol. 422.

Mattick, J., "The Human Genome and the Future of Medicine," Med. J. Aust., 2003, 212-216, vol. 179.

Ayoubi, P. et al., "PipeOnline 2.0: Automated EST Processing and Functional Data Sorting," Nucleic Acids Research, 2002, 4761-4769, vol. 30, No. 21.

van't Veer Supplementary Information Table 3; Downloaded from nature.com/nature/journal/v415/n6871/suppinfo/415530a.html; Downloaded on Jul. 8, 2008.

"BLAST Search Result 1", Downloaded from NCBI website on Jul. 8, 2008.

GenBank accession No. AA486403 published on Mar. 6, 1998 or earlier; downloaded from http://www.ncbi.nlm.nih.gov/entrez/viewer.fcgi?2216567:EST:1131978; downloaded on Jul. 16, 2007.

GenBank accession No. AA454543 published on Jun. 6, 2007; downloaded from http://www.ncbi.nlm.nih.gov/entrez/viewer.fcgi?2177319:EST:1099098; downloaded on Jul. 16, 2007.

GenBank accession No. R54559 published on May 18, 1995; downloaded from http://www.ncbi.nlm.nih.gov/entrez/viewer.fcgi?816461:EST:224624; downloaded on Jul. 16, 2007.

* cited by examiner

Fig. 5
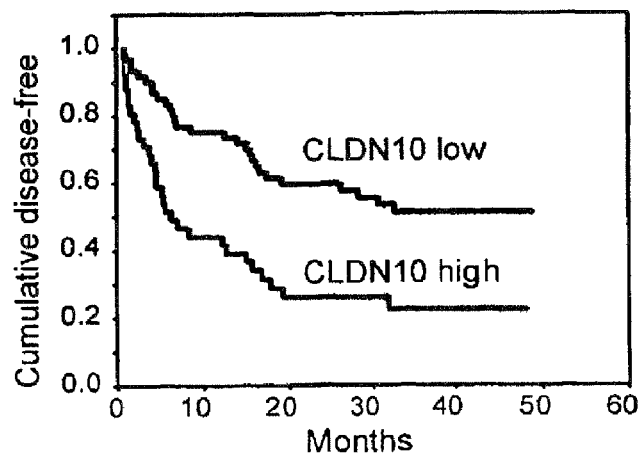
A  All patients
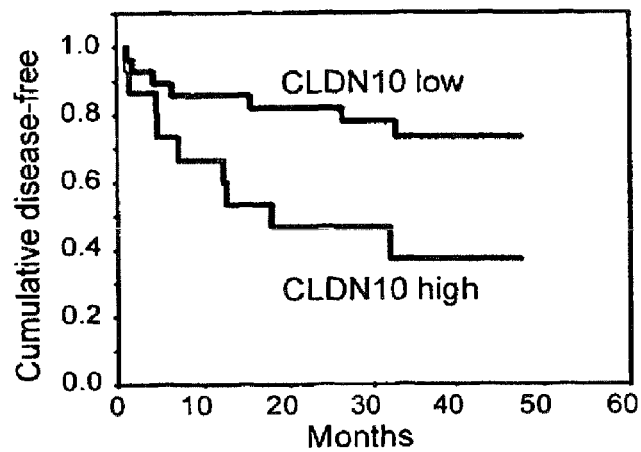
B  Early stage patients
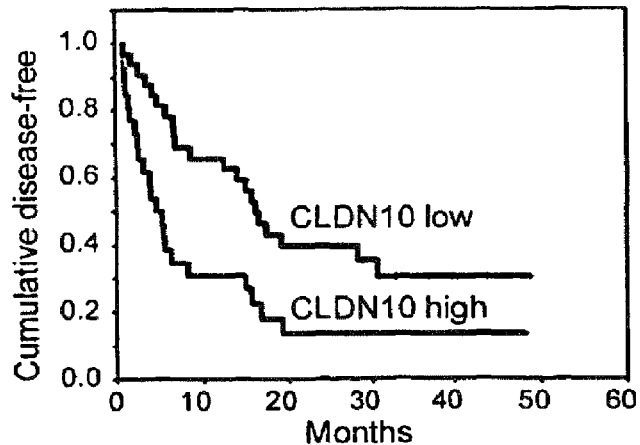
C  Late stage patients

Fig. 7
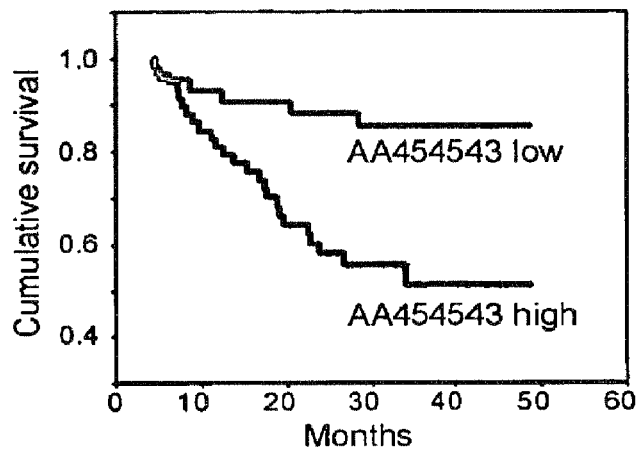
A All patients
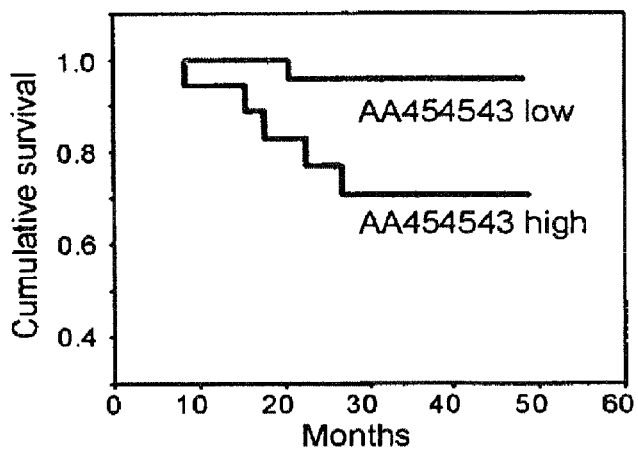
B Early stage patients
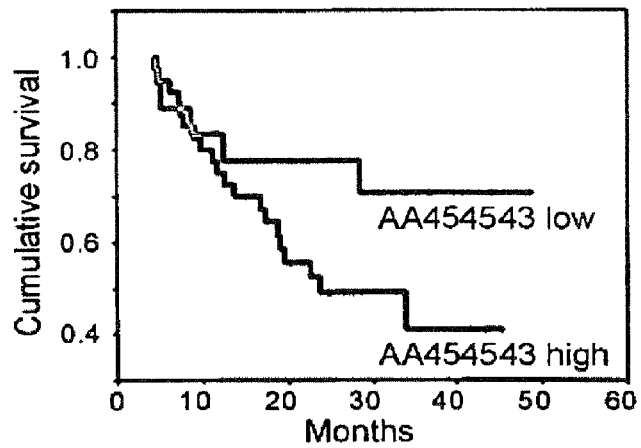
C Late stage patients

COMPOSITIONS AND METHODS FOR PROGNOSIS AND THERAPY OF LIVER CANCER

CROSS-REFERENCE TO RELATED APPLICATIONS

This application is a divisional of U.S. application Ser. No. 10/917,195, filed Aug. 12, 2004, now abandoned which claims the benefit of U.S. provisional application Ser. No. 60/494,981, filed Aug. 13, 2003, and Ser. No. 60/500,844, filed Sep. 4, 2003, which are hereby incorporated by reference in their entirety.

Throughout this application, various publications are referenced. Full citations for these publications may be found immediately preceding the claims. The disclosures of these publications are hereby incorporated by reference into this application in order to more fully describe the state of the art as of the date of the invention described and claimed herein.

BACKGROUND OF THE INVENTION

Hepatocellular carcinoma (HCC) is a common lethal malignancy and among the five leading causes of cancer death worldwide. The incidence is rising in the United States, UK and Japan. Liver cancer is the second major cause of cancer death in China. Epidemiological studies have shown that hepatitis B and C virus infections, alcohol-induced liver injury and consumption of aflatoxin are closely associated with liver cancer. Extensive studies have been performed to better understand the clinico-pathological features to improve the clinical management for HCC patients. However, conventional clinico-pathological parameters have limited predictive power, and patients with the same stage of disease can have very different disease outcomes. Microarray technology provides a biological mean to gather large amount of gene expression data on an unbiased basis. Molecular portraits reviewed by the tumors' gene expression patterns have been used to identify new molecular criteria for prognostication of diverse cancer types including breast cancer, prostate cancer, lung cancer and brain tumors.

Using the cDNA microarray approach, the expression profiles of liver cancer cell lines and human samples have been reported. Expression of alpha-fetoprotein (AFP) highlighted the molecular subtypes of HCC cell lines. Deregulation of the cell cycle regulators and genes associated with metabolism have been observed, and the expression profile was associated with the tumor differentiation status. A recent study on prediction of HCC early recurrence by gene expression only reported the intrahepatic recurrence within 1 year in a small patient set and used genechips of 6000 genes. In the present study, the Cox regression and Kaplan-Meier analyses were used on 48 HCCs to identify a set of 26 genes from microarrays printed with 23000 clones. The prognostic gene set was then further delineated to include the top ranked 12 genes, which had an accuracy of 97.8% and 89.3% in predicting disease recurrence and death, respectively, within 3 years after hepatectomy. The gene expression profile thus generated can provide a more accurate prognosis to predict disease recurrence and death compared to the standard systems based on clinical and histological criteria. The result also offers an approach to select patients with poor prognosis for aggressive adjuvant therapy.

SUMMARY OF THE INVENTION

This invention provides a composition comprising the following polynucleotide probes: IL7R (AA485865) (SEQ ID NO:7), NDRG1 (AA486-403) (SEQ ID NO:8), EST1 (H50345) (SEQ ID NO:9), TRPC1 (AA017132) (SEQ ID NO:10), GFRA1 (AA512935) (SEQ ID NO:11), EST2 (AA454543) (SEQ ID NO:12), CLDN10 (R54559) (SEQ ID NO:13), DNALI1 (R93087) (SEQ ID NO:14), RBP5 (AA453198) (SEQ ID NO:15), EST3 (AA621761) (SEQ ID NO:16), EST4 (63706) (SEQ ID NO:17), PCOLCE (AA670200) (SEQ ID NO:18), TDO2 (T72398) (SEQ ID NO:19), EST5 (T47454) (SEQ ID NO:20), HIST1H2BD (N33927) (SEQ ID NO:21), PXMP2 (N70714) (SEQ ID NO:22), ACAS2 (AA455146) (SEQ ID NO:23), ANAPC7 (T68445) (SEQ ID NO:24), EST6 (AA576580) (SEQ ID NO:25), RBP5 (N92148) (SEQ ID NO:26), ANXA1 (H63077) (SEQ ID NO:27), CKB (AA894557) (SEQ ID NO:28), ITGBL1 (N52533) (SEQ ID NO:29), KPNA2 (AA676460) (SEQ ID NO:30), EST7 (W90740) (SEQ ID NO:31) and MEG3 (W85841) (SEQ ID NO:32), or any combination thereof.

This invention further provides a composition comprising the following polynucleotide probes: IL7R (AA485865) (SEQ ID NO:7), NDRG1 (AA486-403) (SEQ ID NO:8), EST1 (H50345) (SEQ ID NO:9), TRPC1 (AA017132) (SEQ ID NO:10), GFRA1 (AA5±2935) (SEQ ID NO:11), EST2 (AA454543) (SEQ ID NO:12), CLDN10 (R54559) (SEQ ID NO: 13), DNALI1 (R93087) (SEQ ID NO:14), RBP5 (AA453198) (SEQ ID NO:15), EST3 (AA621761) (SEQ ID NO:16), EST4 (N63706) (SEQ ID NO:17) and PCOLCE (AA670200) (SEQ ID NO:18).

This invention provides a method for determining the likelihood of recurrence of hepatocellular carcinoma (HCC) in a subject afflicted with HCC, comprising: (a) obtaining a tumor sample from the subject; (b) determining the gene expression pattern of a set of prognostic genes in the tumor sample; (c) calculating the prognostic gene score of the gene expression pattern; and (d) comparing the prognostic gene score to a prognostic gene score associated with recurrence of HCC, thereby determining the likelihood of recurrence of HCC in the subject.

This invention provides a method for determining the likelihood of hepatocellular carcinoma (HCC) to cause the death of an afflicted subject, comprising: (a) obtaining a tumor sample from the subject; (b) determining the gene expression pattern of a set of prognostic genes in the tumor sample; (c) calculating the prognostic gene score of the gene expression pattern; and (d) comparing the prognostic gene score to a prognostic gene score associated with HCC-associated death, thereby determining the likelihood of death of the subject.

This invention also provides a method of determining whether to administer adjuvant therapy for a subject afflicted with hepatocellular carcinoma (HCC) comprising: (a) obtaining a tumor sample from the subject; (b) determining the gene expression pattern of a set of prognostic genes in the tumor sample; and (c) calculating the prognostic gene score of the gene expression pattern; and (d) comparing the prognostic gene score to a prognostic gene score associated with recurrence of HCC, thereby determining whether to administer adjuvant therapy.

This invention further provides a method for determining the prognosis of a subject afflicted with hepatocellular carcinoma (HCC), comprising: (a) obtaining a tumor sample from the subject; (b) determining the level of CLDN10 nucleic acid transcript in the tumor sample; (c) comparing the level of CLDN10 nucleic acid transcript from step (b) with the level of CLDN10 nucleic acid transcript in the normal tissue sample, whereby a higher level of CLDN10 nucleic acid transcript in step (b) indicates a poor prognosis.

This invention also provides a method for determining the prognosis of a subject afflicted with hepatocellular carcinoma (HCC), comprising: (a) obtaining a tumor sample from the subject; (b) determining the level of AA454543 nucleic acid transcript in the tumor sample; (c) comparing the level of AA454543 nucleic acid transcript from step (b) with the level of AA454543 nucleic acid transcript in the normal tissue sample, E whereby a higher level of AA454543 nucleic acid transcript in step (b) indicates a poor prognosis.

This invention further provides a method for determining the prognosis of a subject afflicted with hepatocellular carcinoma (HCC), comprising: (a) obtaining a tumor sample from the subject; (b) determining the level of DNALI1 nucleic acid transcript in the tumor sample; (c) comparing the level of DNALI1 nucleic acid transcript from step (b) with the level of DNALI1 nucleic acid transcript in the normal tissue sample, whereby a higher level of DNALI1 nucleic acid transcript in step (b) indicates a poor prognosis.

Finally, this invention provides a method for determining the likelihood of recurrence of hepatocellular carcinoma (HCC) in a subject afflicted with HCC, comprising: (a) obtaining a serum sample from the subject; (b) detecting the presence of a DNALI1 nucleic acid transcript; and (c) determining the polymorphism present at nucleotide 194 of codon 65 of the DNALI1 nucleic acid transcript of step (b) to identify which allele is present, whereby the presence of a T-allele indicates a high probability of recurrence of HCC.

BRIEF DESCRIPTION OF THE FIGURES

FIG. 5 Kaplan-Meier disease-free survival plot. (A) All patients were categorized into low or high claudin-10 expression groups. (B) Early stage (Stages I and II) patients were further segregated according to claudin-10 expression level. (C) Late stage (Stages III and IVa) patients were further segregated according to claudin-10 expression level.

FIG. 7 Kaplan-Meier overall survival plot. (A) All patients were categorized into low or high transcript AA454543 expression groups. (B) Early stage (Stages I and II) patients were further segregated according to transcript AA454543 expression level. (C) Late stage (Stages III and IVa) patients were further segregated according to the transcript AA454543 expression level.

DETAILED DESCRIPTION OF THE INVENTION

Definitions

Figure 1:
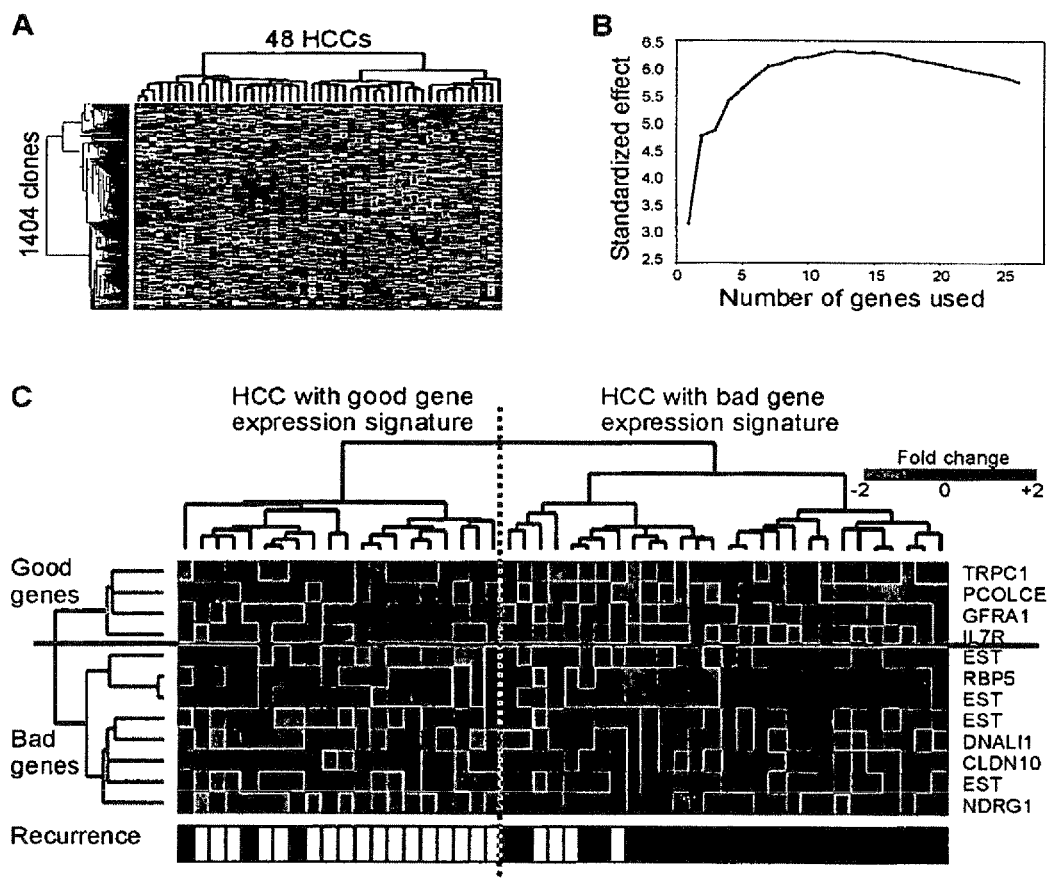
FIG. 1 Gene expression and patients outcome. (A) The global expression data matrix for the 48 HCCs. There were 1404 cDNA clones with significant expression difference among the samples. Each column represented a tumor and each row a single gene. The genes were clustered based on their expression pattern similarities measured over the samples using hierarchical clustering algorithm. Similarly, the samples were clustered based on their similarities over the gene expression pattern. (B) Optimal gene set determination: maximum standardized effect was plotted against the number of genes used to include in the prognostic gene score. (C) Expression data matrix of the 12 prognostic genes for 48 HCCs. The gene name was labeled at the right end of each row. All the "good" genes, with relative risk less than one and expression in high level associated with longer disease-free period, clustered into one branch at the upper panel. The "bad" genes, with relative risk greater than 1 and high level of expression associated with shorter disease-free period, were all clustered into another branch at the lower panel. Similarly, the HCCs were clustered based on their similarities over the expression level of these genes, and were segregated into two major groups. The HCCs at the left side of the plot showed up-regulation of good genes and down-regulation of bad genes, and they were considered to demonstrate the "good prognosis signature". The HCCs at the right side of the plot showed up-regulation of bad genes and down-regulation of good genes, and they were considered to exhibit the "bad prognosis signature". Black box at the bottom of the data matrix indicated the event of recurrence. Solid line, gene prognosis classifier. Dashed line, patient prognosis classifier.

As used in this application, except as otherwise expressly provided herein, each of the following terms shall have the meaning set forth below.

As used herein, "subject" shall mean any animal, such as a primate, mouse, rat, guinea pig or rabbit. In the preferred embodiment, the subject is a human.

As used herein, "composition" shall mean a set of prognostic genes.

As used herein, "hybridizable array elements", shall mean any strand of nucleic acid capable of binding with a complimentary strand of nucleic acid through base pairing.

As used herein, a "gene expression pattern" shall mean a set of values representing nucleic acid levels of a set of prognostic genes.

As used herein, a "prognostic gene score" is a statistical means of evaluating a gene expression pattern. The prognostic gene score is generated based on the proportion of genes in the gene set that demonstrated expression levels associated with poor prognosis. For genes that high level of expression was associated with poor prognosis (bad gene, relative risk greater than 1), the expression level higher than the mean expression value was assigned with 1 point (expression level lower than the mean value had 0 point score). For genes that high level of expression was associated with good prognosis (good gene, relative risk less than 1), the expression level lower than the mean expression value was assigned with 1 point (expression level higher than the mean value scored 0 point). The prognostic gene score for each individual was therefore the average score of all the genes (total points earned/total number of genes investigated). The prognostic gene score of 1, high level of expression for all the bad genes and low level of expression for all the good genes, is suggestive of poor prognosis. Similarly, the prognostic gene score of 0 is indicating good prognosis.

EMBODIMENTS OF THE INVENTION

This invention further provides a composition comprising the following polynucleotide probes: IL7R (AA485865) (SEQ ID NO:7), NDRG1 (AA486-403) (SEQ ID NO:8), EST1 (H50345) (SEQ ID NO:9), TRPC1 (AA017132) (SEQ ID NO:10), GFRA1 (AA512935) (SEQ ID NO:11), EST2 (AA454543) (SEQ ID NO: 12), CLDN10 (R54559) (SEQ ID NO:13), DNALI1 (R93087) (SEQ ID NO:14), RBP5 (AA453198) (SEQ ID NO:15), EST3 (AA621761) (SEQ ID NO:16), EST4 (N63706) (SEQ ID NO:17), PCOLCE (AA670200) (SEQ ID NO:18), TDO2 (T72398) (SEQ ID NO:19), EST5 (T47454) (SEQ ID NO:20), HIST1H2BD (N33927) (SEQ ID NO:21), PXMP2 (N70714) (SEQ ID NO:22), ACAS2 (AA455146) (SEQ ID NO:23), ANAPC7 (T68445) (SEQ ID NO:24), EST6 (AA576580) (SEQ ID NO:25), RBP5 (N92148) (SEQ ID NO:26), ANXA1 (H63077) (SEQ ID NO:27), CKB (AA894557) (SEQ ID NO:28), ITGBL1 (N52533) (SEQ ID NO:29), KPNA2 (AA676460) (SEQ ID NO:30), EST7 (W90740) (SEQ ID NO:31) and MEG3 (W85841) (SEQ ID NO:32), or any combination thereof.

In one embodiment, the polynucleotide probes are complementary DNAs. In another embodiment, the polynucleotide probes are clone cDNAs. The polynucleotide probes may be immobilized on a substrate and may be hybridizable array elements.

This invention provides a composition comprising the following polynucleotide probes: IL7R (AA485865) (SEQ ID NO:7), NDRG1 (AA486-403) (SEQ ID NO:8), EST1 (H50345) (SEQ ID NO:9), TRPC1 (AA017132) (SEQ ID NO:10), GFRA1 (AA512935) (SEQ ID NO:11), EST2 (AA454543) (SEQ ID NO:12), CLDN10 (R54559) (SEQ ID NO:13), DNALI1 (R93087) (SEQ ID NO:14), RBP5 (AA453198) (SEQ ID NO:15), EST3 (AA621761) (SEQ ID NO:16), EST4 (N63706) (SEQ ID NO:17), and PCOLCE (AA670200) (SEQ ID NO:18).

In a preferred embodiment, this invention further provides a composition comprising the following polynucleotide probes: IL7R (AA485865) (SEQ ID NO:7), NDRG1 (AA486-403) (SEQ ID NO:8), EST1 (H50345) (SEQ ID NO:9), TRPC1 (AA017132) (SEQ ID NO:10), GFRA1 (AA512935) (SEQ ID NO:11), EST2 (AA454543) (SEQ ID NO:12), CLDN10 (R54559) (SEQ ID NO:13), DNALI1 (R93087) (SEQ ID NO:14), RBP5 (AA453198) (SEQ TD NO:15), EST3 (AA621761) (SEQ ID NO:16), EST4 (N63706) (SEQ ID NO:17), PCOLCE (AA670200) (SEQ ID NO:18), and one or more of the following nucleotide probes: TDO2 (T72398) (SEQ ID NO:19), EST5 (T47454) (SEQ ID NO:20), HIST1H2BD (N33927) (SEQ ID NO:21), PXMP2 (N70714) (SEQ ID NO:22), ACAS2 (AA455146) (SEQ ID NO:23), ANAPC7 (T68445) (SEQ ID NO:24), EST6 (AA576580) (SEQ ID NO:25), RBP5 (N92148) (SEQ ID NO:26), ANXA1 (H63077) (SEQ ID NO:27), CKB (AA894557) (SEQ ID NO:28), ITGBL1 (N52533) (SEQ ID NO:29), KPNA2 (AA676460) (SEQ ID NO:30), EST7 (W90740) (SEQ ID NO:31) and MEG3 (W85841) (SEQ ID NO:32).

In one embodiment, the polynucleotide probes are complementary DNAs. In another embodiment, the polynucleotide probes are clone cDNAs. The polynucleotide probes may be immobilized on a substrate and may be hybridizable array elements.

This invention further provides a method for determining the likelihood of recurrence of hepatocellular carcinoma (HCC) in a subject afflicted with HCC, comprising: (a) obtaining a tumor sample from the subject; (b) determining the gene expression pattern of a set of prognostic genes in the tumor sample; (c) calculating the prognostic gene score of the gene expression pattern; and (d) comparing the prognostic gene score to a prognostic gene score associated with recurrence of HCC, thereby determining the likelihood of recurrence of HCC in the subject.

In a preferred embodiment of the instant method, expression pattern is determined by microarray. In another embodiment, the gene expression pattern is determined by RT-PCR.

In a preferred embodiment of the instant method, a prognostic gene score of less than 0.416 indicates a low probability of recurrence of HCC, and a prognostic gene score of at least 0.416 indicates a high probability of recurrence of HCC.

This invention further provides a method for determining the likelihood of hepatocellular carcinoma (HCC) to cause the death of an afflicted subject, comprising: (a) obtaining a tumor sample from the subject; (b) determining the gene expression pattern of a set of prognostic genes in the tumor sample; (c) calculating the prognostic gene score of the gene expression pattern; and (d) comparing the prognostic gene score to a prognostic gene score associated with death caused by HCC, thereby determining the likelihood of HCC-associated death of the subject.

In a preferred embodiment of the instant method, a prognostic gene score of less than 0.600 indicates a low probability of HCC-associated death, and a prognostic gene score of at least 0.600 indicates a high probability of HCC-associated death.

This invention further provides a method of determining whether to administer adjuvant therapy for a subject afflicted with hepatocellular carcinoma (HCC) comprising: (a) obtaining a tumor sample from the subject; (b) determining the gene expression pattern of a set of prognostic genes the tumor sample; and (c) calculating the prognostic gene score of the gene expression pattern; and (d) comparing the prognostic gene score to a prognostic gene score associated with recurrence of HCC, thereby determining whether to administer adjuvant therapy.

In a preferred embodiment of the instant method, a prognostic gene score of less than 0.416 indicates a low probability of recurrence of HCC, and a prognostic gene score of at least 0.416 indicates a high probability of recurrence of HCC.

This invention further provides a method for determining the prognosis of a subject afflicted with hepatocellular carcinoma (HCC), comprising: (a) obtaining a tumor sample from the subject; (b) determining the level of CLDN10 nucleic acid transcript in the tumor sample; (c) comparing the level of CLDN10 nucleic acid transcript from step (b) with the level of CLDN10 nucleic acid transcript in the normal tissue sample, whereby a higher level of CLDN10 nucleic acid transcript in step (b) indicates a poor prognosis.

This invention also provides a method for determining the prognosis of a subject afflicted with hepatocellular carcinoma (HCC), comprising: (a) obtaining a tumor sample from the subject; (b) determining the level of AA454543 nucleic acid transcript in the tumor sample; (c) comparing the level of AA454543 nucleic acid transcript from step (b) with the level of AA454543 nucleic acid transcript in the normal tissue sample, whereby a higher level of AA454543 nucleic acid transcript in step (b) indicates a poor prognosis.

This invention further provides a method for determining the prognosis of a subject afflicted with hepatocellular carcinoma (HCC), comprising: (a) obtaining a tumor sample from the subject; (b) determining the level of DNALI1 nucleic acid transcript in the tumor sample; (c) comparing the level of DNALI1 nucleic acid transcript from step (b) with the level of DNALI1 nucleic acid transcript in the normal tissue sample, whereby a higher level of DNALI1 nucleic acid transcript in step (b) indicates a poor prognosis.

Finally, this invention provides a method for determining the likelihood of recurrence of hepatocellular carcinoma (HCC) in a subject afflicted with HCC, comprising: (a) obtaining a serum sample from the subject; (b) detecting the presence of a DNALI1 nucleic acid transcript; and (c) determining the polymorphism present at nucleotide 194 of codon 65 of the DNALI1 nucleic acid transcript of step (b) to identify which allele is present, whereby the presence of a T-allele indicates a high probability of recurrence of HCC.

Example I

Synopsis

Hepatocellular carcinoma (HCC) patients with the same stage of disease can have remarkable differences in disease outcome. The microarray gene expression profiles of the present study were evaluated by Cox regression and Kaplan-Meier analyses, and identified a set of 12 genes that can provide a more accurate prognostication compared to the conventional clinico-pathological systems. The prognostic gene score for each patient was generated based on the proportion of genes in the optimal gene set that demonstrated expression level associated with poor prognosis. Patients with good and poor prognostic gene score differed significantly, and the prognostic gene score was the independent factor compared with pTNM stage to predict disease recurrence. The set of prognostic genes can help to select patients with poor prognosis for aggressive adjuvant therapy.

Materials and Methods

Patients and Samples

In the present study, the gene expression profiles from 48 patients undergoing curative partial hepatectomy for HCC were included for patient outcome analysis. The patients were excluded from the present disease outcome analysis if pathological examination of the resected specimen showed positive resection margin or mixture of other tumor cell types (e.g. cholangiocarcinoma), if they had received chemotherapy before or after resection, received liver transplantation instead of partial hepatectomy, the resection was for recurrence, or the resection was followed by hospital mortality. Diagnosis of recurrence was based on typical imaging findings in a contrast-enhanced CT scan and an increased serum AFP level. In cases of uncertainty, hepatic arteriography and a post-Lipiodol CT scan were performed, and if necessary, fine-needle aspiration cytology was used for confirmation. Up to the date of analysis (May 2003), 27 patients developed recurrence and the median disease-free period was 4.5 months (range, 0.9-32.7 months), and 17 of them succumbed to disease with median survival period of 12.4 months (rang, 4.5-34.1 months). For the 21 patients who were recurrence-free, the median duration of follow-up was 40.9 months (range, 29.8-48.8 months). Another 47 HCCs were later tested independently by quantitative RT-PCR. In this second sample set, 26 of the patients developed recurrence and median disease-free period was 5.5 months (range, 2.2-19.3 months); for the 21 patients that were disease-free, the median duration of follow-up was 23.3 months (range, 11.5-31.1 months).

Microarray Expression Study

The cDNA microarray slides were printed with about 23,000 cDNA clones. Samples and RNA preparations, and hybridization protocols have been established. A total of 1404 cDNA clones with expression levels that differed by at least four-fold from the mean in at least two samples were selected for further analysis. The hierarchical clustering algorithm was applied both to the genes and arrays using the Pearson correlation coefficient as the measure of similarity. The results were further analyzed with TreeView (Eisen; rana.1-bl.gov)

Quantitative RT-PCR

Quantitative RT-PCR was performed. Human 18s rRNA primer and probe reagents (Pre-Developed TaqMan Assay Reagents, Applied Biosystems, Foster City, Calif.) were used as the normalization control for the subsequent multiplexed reactions. Transcript quantification was performed in triplicates for every sample. Quantification was performed using the ABI Prism 7700 sequence detection system (Applied Biosystems). The primers and probe for the CLDN10 are CLDN10F, 5'-CTGTGGAAGGCGTGCGTTA-3' (SEQ ID NO:1); CLDN10-R, 5'-CAAAGAAGCCCAGGCTGACA-3' (SEQ ID NO:2); and CLDN10-P, 5'-6FAM CCTCCAT-GCTGGCGCMGBNFQ-3' (SEQ ID NO:3).

Prognostic Gene Score

A prognostic gene score for each patient was generated based on the proportion of genes in the gene set that demonstrated expression level associated with poor prognosis. For genes that high level of expression was associated with poor prognosis (bad gene, relative risk greater than 1), the expression level higher than the mean expression value was assigned with 1 point (expression level lower than the mean value had 0 point score). For genes that high level of expression was associated with good prognosis (good gene, relative risk less than 1), the expression level lower than the mean expression value was assigned with 1 point (expression level higher than the mean value scored 0 point) The prognostic gene score for each individual was therefore the average score of all the genes (total points earned/total number of genes investigated). The prognostic gene score of 1, high level of expression for all the bad genes and low level of expression for all the good genes, is suggestive of poor prognosis. Similarly, the prognostic gene score of 0 is indicating good prognosis.

Statistical Methods

To determine the gene set for predicting disease recurrence, the examination of the effect of expression level on each of the 1404 clones on recurrence was performed using Cox regression analysis. Genes with P values less than 0.05 were selected. In the second step, the gene set was further delineated by inclusion of genes whose P values were less than 0.05 when examined by Kaplan-Meier log rank test. To perform the test, the patients were categorized into two groups for each gene datum. The grouping was according to the gene expression level with cut-off at the mean expression value. In the third step, a "step-down" approach was used to determine the optimal gene set with minimal number of genes that could provide the best prediction of recurrence. One gene in the gene set was temporarily removed at a time and a Cox regression analysis was performed on the resulting gene score. The gene was removed from the set when its removal had the maximum standardized effect (i.e. log relative risk/ standard error). The process continued until one gene was left in the set. The number of genes at which the corresponding gene score yielded the highest standardized effect was taken as the optimum. The analysis was programmed by using the macro language in the Statistical Analysis System (SAS) Version 8.2. The accuracy of using a gene score for prediction of recurrence was measured by the area under the receiver operating characteristics (ROC) curve. The prediction power for 3 years was analyzed. Patients who were disease-free but with less than 3 years follow-up were excluded in the prediction study, analyzing 45 patients with 27 of them developed recurrences. Similarly for the survival prediction, analyzing 44 patients with 17 deaths. The Youden index, i.e. the sum of sensitivity and (1-specificity), was used to determine the best cut-off point. The SAS was used for the analysis. The association of clinico-pathological parameters with patient outcome was examined by Cox proportional hazards regression with the forward stepwise selection procedure aided by SPSS version 11.0 software package (SPSS Inc. Chicago, Ill.).

TABLE 1

Disease-free survival univariate analysis for the 26 genes

| Gene name | Accession | Relative Risk | P | Gene rank[a] |
|---|---|---|---|---|
| IL7R | AA485865 | 0.6 (0.4-0.9) | 0.011 | 1 |
| NDRG1 | AA486403 | 1.5 (1.1-2.0) | 0.006 | 2 |
| EST1 | H50345 | 1.7 (1.1-2.6) | 0.011 | 3 |
| TRPC1 | AA017132 | 0.6 (0.4-0.9) | 0.016 | 4 |
| GFRA1 | AA512935 | 0.5 (0.3-0.9) | 0.014 | 5 |
| EST2 | AA454543 | 1.7 (1.2-2.6) | 0.008 | 6 |
| CLDN10 | R54559 | 1.7 (1.1-2.7) | 0.014 | 7 |
| DNALI1 | R93087 | 1.9 (1.2-3.0) | 0.006 | 8 |
| RBP5 | AA453198 | 1.4 (1.0-2.0) | 0.033 | 9 |
| EST3 | AA621761 | 1.7 (1.0-3.0) | 0.049 | 10 |
| EST4 | N63706 | 1.8 (1.1-2.9) | 0.020 | 11 |
| PCOLCE | AA670200 | 0.7 (0.5-0.9) | 0.010 | 12 |
| TDO2 | T72398 | 0.8 (0.6-1.0) | 0.038 | 13 |
| EST5 | T47454 | 0.7 (0.5-1.0) | 0.040 | 14 |
| HIST1H2BD | N33927 | 1.7 (1.1-2.5) | 0.012 | 15 |
| PXMP2 | N70714 | 1.7 (1.1-2.6) | 0.031 | 16 |
| ACAS2 | AA455146 | 1.8 (1.2-2.6) | 0.004 | 17 |
| ANAPC7 | T68445 | 0.7 (0.5-1.0) | 0.024 | 18 |
| EST6 | AA576580 | 1.9 (1.1-3.2) | 0.021 | 19 |
| RBP5 | N92148 | 1.4 (1.0-1.9) | 0.049 | 20 |
| ANXA1 | H63077 | 0.5 (0.3-0.9) | 0.020 | 21 |
| CKB | AA894557 | 1.3 (1.1-1.7) | 0.010 | 22 |
| ITGBL1 | N52533 | 0.7 (0.4-1.0) | 0.048 | 23 |
| KPNA2 | AA676460 | 1.6 (1.0-2.6) | 0.048 | 24 |
| EST7 | W90740 | 0.6 (0.4-0.9) | 0.012 | 25 |
| MEG3 | W85841 | 1.2 (1.0-1.5) | 0.038 | 26 |

[a]The relative importance of the genes for predicting recurrence was ranked by step-down approach.

From the top of each of the first and second column of Table 1, the sequences listed therein are identified by SEQ ID NOs: 7-32, respectively.

Results

Gene Expression Profile

Fluorescence intensities of the scanned images were quantified, normalized and corrected to yield the transcript abundance of a gene as an intensity ratio with respect to that of the mean value of the sample pool. A total of 1404 cDNA clones were significantly regulated across the group of 48 HCC samples with at least four-fold difference in two samples. Using hierarchical clustering algorithm, the 48 HCCs were clustered based on their similarities over the 1404 significant clones. The HCC samples were segregated into two distinct branches (25 and 23 HCCs, respectively) and correlated with the clinico-pathological parameters, such as serum AFP level, size of the tumor, presence of venous infiltration, pTNM stage and recurrence. Twenty-six patients developed recurrence and the median disease-free period was 4.5 months (range, 0.9-32.7 months). For the 22 patients who were recurrence-free, the median duration of follow-up was 37.2 months (range, 26.1-45.4 months). However, none of these clinico-pathological parameters correlated with the global expression signatures. The result was expected as the global gene expression profiles of HCC were associated with the proliferation and metabolic rate of the tumor, and the status of dedifferentiation of the tumor cells.

The 1404 clones were then specifically searched for their association of tumor recurrence among the 48 patients. Cox regression analysis on the gene expression level in association with disease recurrence was evaluated and 54 genes were found to be significantly associated with tumor recurrence (P<0.05, 3.8% of the 1404 significant clones). In the second step to further minimize the number of genes for recurrence prediction, the 54 genes were examined by Kaplan-Meier analysis. Twenty-six genes with P values less than 0.05 by log rank test were identified (Table 1).

A prognostic gene score for each individual patient was generated as described in the method section. The score was based on the proportion of genes in the gene set that demonstrated expression level associated with poor prognosis. A step-down approach was adopted to determine the minimal set of genes that could provide a prognostic gene score with the best prediction of recurrence. The relative importance of the genes for the prediction of recurrence was ranked and the last gene in the order of removal was the most important gene to predict recurrence (Table 1). A graph of the standardized effect against the number of genes considered was plotted (FIG. 1B) The maximum standardized effect was achieved when the number of genes was optimized to the top ranked 12 genes that predict recurrence.

The expression pattern of the 12 genes in the 48 HCC samples was shown (FIG. 1C). The genes were clustered on the basis of their similarities measured over the samples by hierarchical clustering algorithm. In the gene dendrogram two distinct groups of genes were revealed. Notably, the top panel contained the "good" genes with relative risk (RR) less than 1 by Cox analysis. High level of expression of these "good" genes was associated with longer disease-free period by Kaplan-Meier analysis. Genes at the bottom panel were the "bad" genes with RR greater than 1, and expression in high level associated with shorter disease-free period. Similarly, the HCCs were segregated on the basis of their similarities measured over these 12 prognostic genes into two groups with the event of recurrence indicated at the bottom of the data matrix. The HCCs clustered at the left side showed a good gene expression signature with up-regulation of good genes and down-regulation of bad genes. On the contrary, HCCs clustered at the right side exhibited a bad gene expression signature with up-regulation of bad genes and down-regulation of good genes. The majority of patients with bad prognosis signature developed recurrence ($24/28$, 85.7%) compared to low incidence of recurrence in patients with good prognosis signature (3/20, 15%); Fisher's exact test, P<0.001.
Confirmation Using an Independent Set of HCCs.

Figure 2:
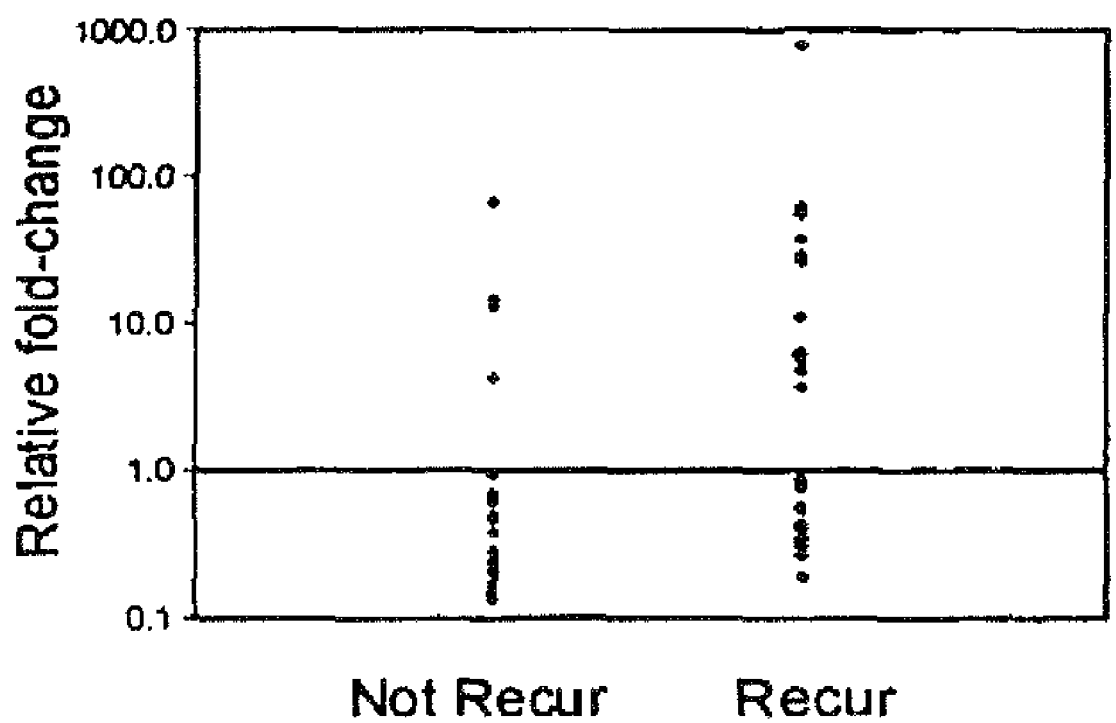
FIG. 2 Validation analysis of CLDN10 gene expression in an independent sample set. Scatter plot of the CLDN10 expression level by quantitative RT-PCR. The expression level of each sample was relative to the median expression value of the sample set. Patients with CLDN10 expression level higher than the median value were indicated in the upper portion of the plot with relative fold-change greater than 1. Patients with gene expression lower than the median value were indicated in the lower portion of the plot with relative fold-change less than 1.
Figure 3:
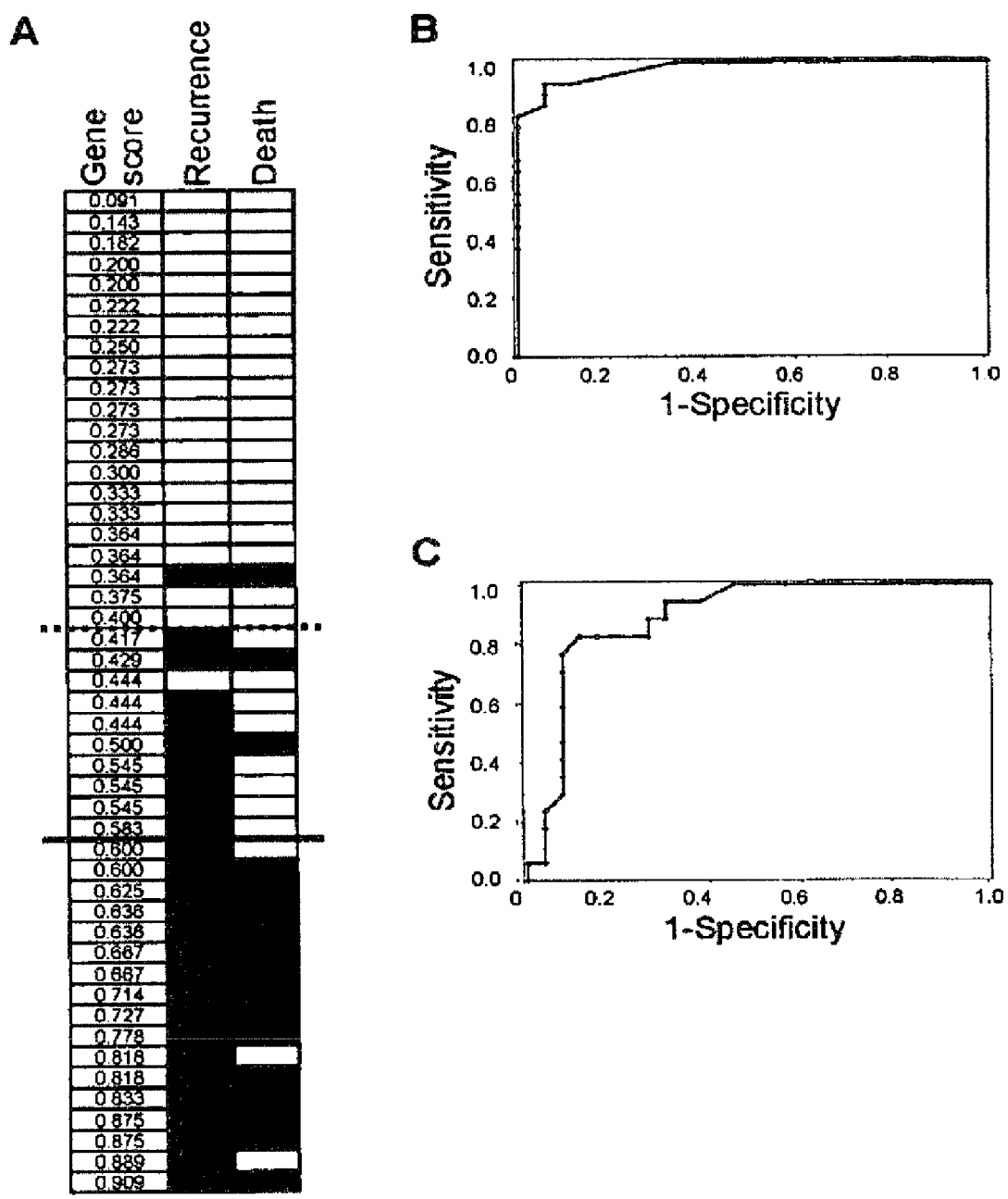
FIG. 3 Prognostication by gene expression. (A) Prognostic gene score based on the 12 top-ranked genes. The optimal cut-off value for prediction of disease recurrence and death was 0.416 (dashed line) and 0.600 (solid line), respectively, as determined by the Youden Index. (B) Receiver operating characteristic (ROC) curve for prediction of recurrence. (C) ROC curve for prediction of death.

To validate the genes for prognosis, a gene was arbitrarily selected from the set of 12 genes to verify the microarray expression data using an additional independent set of primary HCCs. A different experimental method, quantitative RT-PCR, was employed to examine the expression level of claudin 10 (CLDN10). Patients were categorized into two groups by using their median expression value as cut-off. For patients with high level of CLDN10 expression, 14 of 18 patients (77.8%) developed recurrence; whereas 12 of 29 patients (41.4%) with low level of expression developed recurrence (Fisher's exact test, P=0.015) (FIG. 2). High level of CLDN10 expression was associated with increased risk of disease recurrence; the RR was 3-fold (95% confidence interval (CI), 1.4-6.6; P=0.006). By Kaplan-Meier analysis, the median disease-free survival period was 5.5 months in patients with high CLDN10 level compared to >17.5 months in patients with low level of expression (log rank test, P=0.004). Thus, the microarray and RT-PCR showed comparable results on CLDN10 in the validation sample set.
Gene Expressions and Clinico-Pathological Features The prognostic gene score based on the optimal set of 12 genes was ranked and compared with patient outcome (FIG. 3A). The accuracy of patient outcome prediction by prognostic gene score was measured by the area under the receiver operating characteristic (ROC) curve. The accuracy for recurrence prediction within 3 years was 97.8% (CI 95%, 94.8-100%) (FIG. 3B). The best cut-off value for recurrence prediction was 0.416 as determined by the Youden Index. The specificity and sensitivity of predicting recurrence within 3 years was 94.4% (95% CI, 72.7-99.9%) and 92.6% (95% CI, 75.7-99.1%), respectively. The estimated RR for the development of recurrence in 3 years was 57.7-fold. The prediction accuracy for patients succumbed to disease was 89.3% (CI 95%, 79.4-99.2%) by ROC curve (FIG. 3C). The optimal cut-off value for survival prediction was 0.600 by the Youden Index. The specificity and sensitivity of predicting death within 3 years was 88.9% (95% CI, 70.8-97.7%) and 82.4% (95% CI, 56.6-96.2%), respectively. The estimated RR for death in 3 years was 16.9-fold.

The correlation of clinico-pathological characteristics with HCC recurrence was analyzed (Table 2). The presence of venous invasion, tumor size larger than 5 cm, and late pTNM stages were all significantly associated with disease recurrence. These 3 features and the presence of microsatellite nodules were significantly associated with disease death. Gender, age, HBV infection history, serum level of AFP, cirrhosis of liver, tumor encapsulation, and Edmondson grade were not significantly associated with recurrence nor death. As suggested by the RR, the prognostic gene score outperformed all the clinico-pathological parameters.

TABLE 2

Disease-free and overall survival univariate analysis for gene score and clinico-pathological parameters

| Variables[a] | Disease-free survival Relative Risk | P | Overall survival Relative Risk | P |
|---|---|---|---|---|
| Gene score | 57.7 (7.6-435.9) | <0.001 | 16.9 (4.8-60.2) | <0.001 |
| Venous infiltration | 2.2 (1.0-4.8) | 0.039 | 2.9 (1.1-7.9) | 0.035 |
| Tumor size | 2.7 (1.2-6.0) | 0.013 | 6.9 (2.0-24.2) | 0.002 |
| pTNM stage | 2.4 (1.1-5.4) | 0.032 | 5.4 (1.5-18.7) | 0.008 |
| microsatellite | | 0.285 | 2.8 (1.0-7.7) | 0.043 |

[a]For each variables, the patients were categorized into two groups. The cut-off for tumor size was 5 cm. The insignificant variables with P > 0.05 were not listed in the table including gender, age (cut-off at 60 years old), HBV infection history, serum AFP level (cut-off at 20 ng/ml), cirrhosis liver, tumor encapsulation and Edmondson grade.

Prognosis by Gene Score and pTNM Stage.

The best cut-off value for recurrence and death prediction was different. For overall patient outcome assessment, therefore, we recommended to use prognostic gene score to categorize patients into 3 groups: Gene score A (<0.416) patients with good prognosis, where majority were disease-free and alive in 3 years, with 1/21 (4.8%) recurrence and death; Gene score B (0.416-0.600) patients with intermediary prognosis, where majority developed late recurrence but were still alive in 3 years, with 9/10 (90%) recurrence (median disease-free period was 16.1 months) and 2/10 (20%) death; Gene score C (>0.600) patients with poor prognosis, where majority developed early recurrence and die within 3 years, with 17/17 (100%) recurrence (median disease-free period was 2.5 months) and 14/17 (82.4%) deaths (median overall survival period was 13.7 months).

The prognostic gene score (3 category: score A, B and C) and pTNM stage were compared (4 stage: I, II, III and IVa) by Cox regression analysis of these two factors with the forward stepwise selection procedure. Both prognostic gene score and pTNM stage were independent indicators of poor prognosis. The relative risk for disease-free survival for the prognostic gene score and pTNM stage were 5.7 (95% CI 3.2-10.4, P<0.001) and 1.7 (95% CI 1.0-2.8, P=0.036), respectively. The relative risk for overall survival for the prognostic gene score and pTNM stage were 5.4 (95% CI 2.4-14.0, P<0.001) and 2.0 (95% CI 1.1-3.4, P=0.020), respectively.

Figure 4:
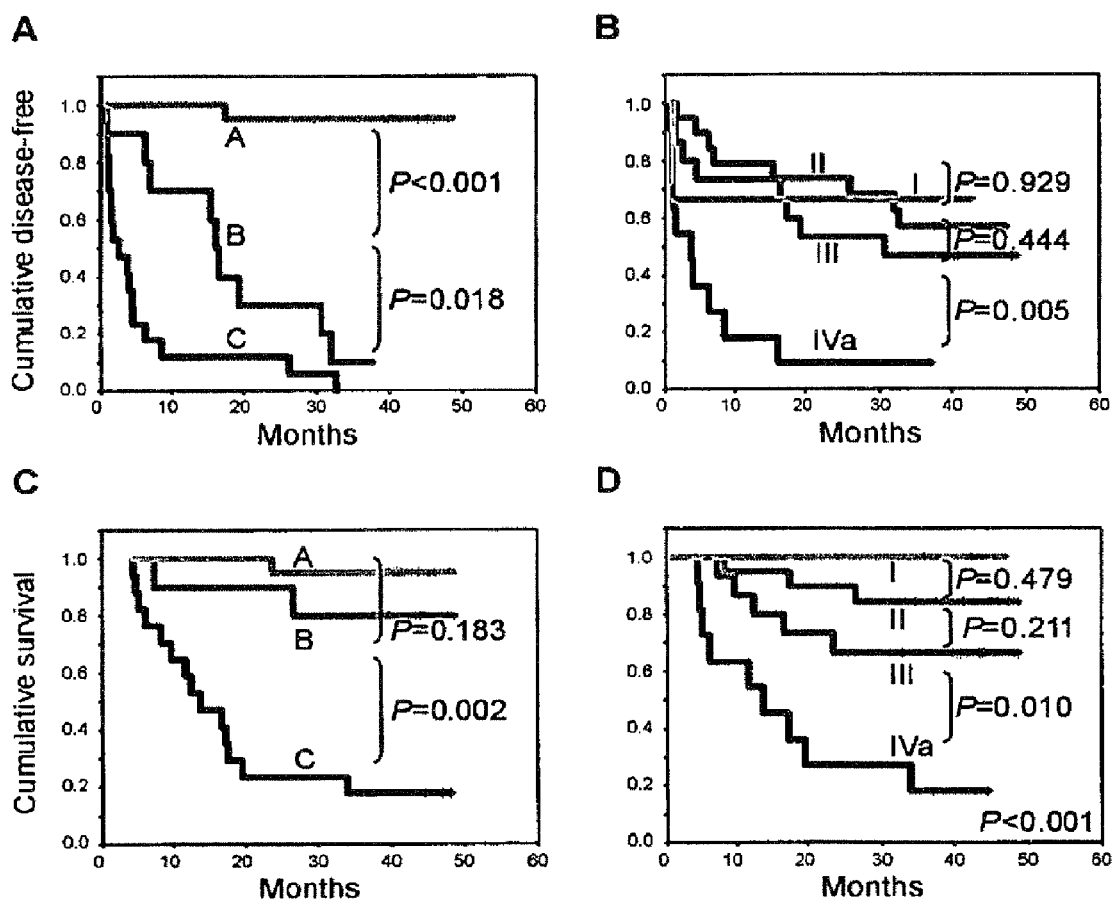
FIG. 4 Comparison between prognostic gene score and pTNM system. Kaplan-Meier disease-free and overall survival curves for the HCC patients according to prognostic gene score in (A) and (C), and pTNM staging system in (B) and (D). In each case, P values were calculated using the log rank test.

The prognostic gene score and pTNM stage were further examined by Kaplan-Meier analysis (FIG. 4). Patients with different prognostic gene score differed significantly in disease-free and overall survival (log rank test P<0.05). In the overall survival analysis between score A and B patients where majority of them were still alive, no significant difference was observed between the 2 groups; nonetheless, as majority of score B patients had developed recurrence within 3 years, the overall survival outcome will be expected to be inferior than the score A patients with longer follow-up. However, patients with different pTNM stage did not differed significantly in disease-free and overall survival. Comparing stage I against II, or stage II against III, no significant difference was observed. Only stage III patients were significantly different from the stage IVa patients. Therefore, prognostic gene score can provide a more accurate prognosis segregation compared to the pTNM staging system.

Discussion

These results indicate that prognosis for HCC patients can be derived from the gene expression profile of the primary tumors. The optimal gene set to predict recurrence was delineated to be the top ranked 12 genes of the 26 genes that were significantly associated with recurrence. Although the prognostic gene set was determined by the association with recurrence event, the result was also applicable for overall survival prediction. The prognostic gene score thus generated had accuracy of 97.8% and 89.3%, respectively, for predicting recurrence and death within 3 years. The prediction power of prognostic gene score outperformed all the clinico-pathological parameters as suggested by the relative risk. Multivariate analysis indicated that prognosis by gene score was independent of pTNM stages. Therefore, gene expression data together with clinical and pathology data will definitely provide a more accurate prediction for disease outcome.

This is the first report on gene expression profile for prediction of disease-free and overall survival in HCC patients after hepatectomy. The current study accounted for both intra- and extra-hepatic recurrence within 3 years, as recurrence outside the liver was also important for disease management and the longer follow-up period would have included majority of recurrence after curative surgery. The fundamental difference in clinical endpoint consideration may account for the prognostic gene list difference between the two reports. However, the discrepancy may also due to the different microarrays used in the two centers, which had included different gene sets in the genechips. Furthermore, patients were mostly HCV-related in Iizuka et al study, whereas majority of our patients were HBV-related, and therefore disease progression may actually involve different genes.

The functional annotation of the genes provides insight into the underlying biological mechanism leading to rapid recurrence. Genes potentially involved in cell invasion and metastasis are significantly up-regulated in the poor prognosis group. For example, CLDN10 family members have been shown to facilitate invasion and migration; dynein, axonemal, light intermediate polypeptide 1 (DNALI1) is a motor protein and may regulate cell migration/motility.

Recent reviews showed that neoadjuvant and adjuvant therapy for localized HCC after curative surgery have modest improvement on overall or disease-free survival. The frustration is expected because about half of the patients would not have developed disease recurrence (FIG. 4A) even without adjuvant treatment. These good prognosis patients may not benefit from the adjuvant treatment but may potentially succumb to the side effects of the adjuvant treatment. Therefore, the prognostic gene score can help to select those high-risk patients who would benefit from adjuvant therapy, and significantly reduce the number of patients who do not require the treatments at all. Furthermore, genes that are deregulated in cancer with poor prognosis are potential targets for the rational development of new cancer drugs and therapeutic targets. In this study, RBP5 was down-regulated in a subset of HCC patients (FIG. 1C) and therefore they could be candidates for chemoprevention by retinoic acid. Patients showing a high level of RBP5 may imply non-responsiveness to retinoic acid, or measures have to be taken to bring down the level of RBP5 for treatment. Identification of these targets may improve the efficacy of developing treatments for other cancers as well.

These results indicate that the prognostic gene score based on expression pattern of 12 genes can accurately predict disease recurrence and survival of HCC patients after curative surgery, and implies that the invasive and metastasis behavior is the biological nature initiated in the primary tumor.

Example II

Synopsis

Hepatocellular carcinoma (HCC) patients with the same clinico-pathological features can have remarkably different disease outcomes after curative hepatectomy. To address this issue, the cDNA microarray gene expression profiles of HCCs were evaluated and identified that claudin-10 expression level was associated with disease recurrence. The aim of this study was to validate the above microarray data by alternative research method applicable for routine practice. Quantitative RT-PCR was employed to validate the microarray data on claudin-10 expression level. The assay was repeated on a separate HCC sample set, to consolidate the prognostic significance of claudin-10. Claudin-10 expression level by quantitative RT-PCR and by microarray measurement showed a high concordance (r=0.602, P<0.001). Quantitative RT-PCR was repeated on a separate HCC sample set and the association of claudin-10 expression with recurrence was again confirmed (hazard ratio 1.2, 95% CI 1.0-1.4, P=0.011). By multivariable Cox regression analysis, claudin-10 expression and pTNM stage were independent factors for prediction of disease recurrence. Claudin-10 expression of HCC can therefore be used as a molecular marker for disease recurrence after curative hepatectomy.

Materials and Methods:

Patients and Samples

Gene expression profiles from 48 patients undergoing curative partial hepatectomy for HCC during the period March 1999 to April 2000 at Queen Mary Hospital, Hong Kong, were included for patient outcome analysis. Patients were excluded from the present disease outcome analysis if the pathological examination of the resected specimen showed positive resection margin or mixture of other tumor cell types (e.g. cholangiocarcinoma); if they had received chemotherapy before or after resection; if they had undergone liver transplantation instead of partial hepatectomy; if the resection was for recurrence or palliative intent; or if the resection was followed by hospital death. Another 53 HCCs operated during the period April 2000 to March 2002 in the same institute with the same exclusion criteria were recruited for validation study. Informed consents had been obtained for specimen collection. The study protocol was approved by the Ethics Committee of the University of Hong Kong.

Diagnosis of HCC recurrence was based on typical imaging findings in a contrast-enhanced computed tomography scan and an increased serum AFP level. In case of uncertainty, hepatic arteriography and a post-Lipiodol computed tomography scan were performed, and if necessary, fine-needle aspiration cytology was used for confirmation. Up to the date of analysis, 59 out of the total 101 patients developed recurrence and the median disease-free period was 5.7 months (range, 0.9-32.7 months). For the remaining 42 patients who were disease-free, the median follow-up period was 34.0 months (range, 14.9-48.8 months). The age of the patients ranged from 13 to 79, with a median age of 52 years. There were 81 men and 20 women. Serum hepatitis B surface antigen (HBsAg) was 5 positive in 92 patients (91.1%). Tumors were staged according to the UICC pTNM tumor classification 1997 version (18), because the 2002 version did not clearly stratify the patients into different stages in terms of survival rate (19). The clinico-pathological features were prospectively collected into the HCC clinical database.

Microarray Expression Study

The cDNA microarray slides were printed with about 23,000 cDNA clones including 17,400 genes. Samples, RNA preparations, and hybridization protocols had been established and described in detail previously (14,20) Data were deposited into the Stanford Microarray Database (21). The fluorescence signals were normalized by mean-centering genes for each array, and then mean-centering each gene across all arrays. Only well measured genes were included in subsequent analyses, and defined as genes that had a ratio of signal intensity to background noise of more than 1.5 fold and net signal intensity to background of more than 50 unit, for either the Cy5-labeled sample or the Cy3-labeled reference, in at least 50 percent of the tested samples. A total of 1,404 cDNA clones with expression levels different by at least four-fold from the mean in at least two samples were selected for further Cox regression analyses.

Quantitative RT-PCR

Quantitative RT-PCR was performed. Human 18s rRNA primer and probe reagents (Pre-Developed TaqMan Assay Reagents, Applied Biosystems, Foster City, Calif.) were used as the normalization control for subsequent multiplexed reactions. The relative amount of claudin-10, which had been normalized with control 18s for RNA amount variation and calibrator for plate-to-plate variation, was presented as the relative fold change in log 2 base. Transcript quantification was performed in at least triplicates for every sample. Quantification was performed using the ABI Prism 7700 sequence detection system (Applied Biosystems). Primers and probe for claudin-10 were CLDN10-F, 5'-CTGTG GAAGG CGTGC GTTA-3' (SEQ ID NO:1); CLDN10-R, 5'-CAAAG AAGCC CAGGC TGACA-3' (SEQ ID NO:2); and CLDN10-P, 5'-6FAM CCTCC ATGCT GGCGC MGBNFQ-3' (SEQ ID NO:3).

Statistical Methods

Cox regression analyses with gene expression data as continuous variables were computed to examine gene expression that was associated with disease recurrence after curative resection. The technical concern of microarray data reproducibility was addressed by using quantitative RT-PCR for validation. Expression data by microarray and quantitative RT-PCR data were continuous variables assessed by Pearson's correlation coefficient (r). The association of claudin-10 expression and disease-free survival was validated in another independent sample set, and we employed quantitative RT-PCR as a different assay technique for the transcript quantitation in the independent sample set.

The claudin-10 expression data was modeled as categorical variable only in the Kaplan-Meier analyses. The Youden index (sensitivity+specificity −1) (23) was used to determine the optimal cut-off point of claudin-10 expression for the prediction of 3-year disease-free survival. Other cut-off values including the mean, median and 75th percentile had also been considered and examined, and they were all able to segregate the patients with clinical implications. The Youden index was employed to maximize the sensitivity and specificity of the prediction simultaneously.

The association of gene expression and clinico-pathological parameters with patient outcome was examined by a multivariable Cox proportional hazards regression with the forward stepwise selection procedure. The claudin-10 expression data was modeled as continuous variable, and all the clinico-pathological parameters were modeled as categorical variables in the Cox regression analyses. The associations of claudin-10 expression level with clinico-pathological features were assessed by Spearman correlation and Mann-Whitney U test where appropriate. Differences were considered significant when P value was less than 0.05. The statistical analyses were aided by SPSS version 11.0 software package (SPSS Inc., Chicago, Ill.).

Additional Microarray Information

The microarray study was carried out following the MIAME guidelines issued by the Microarray Gene Expression Data Group (24). The original data are available in the Stanford Microarray Database (genome-www5.stanford.edu). Information is also available from the authors on request.

Results:

Claudin-10 Expression and Recurrence

Cox regression analyses with gene expression modeled as a continuous variable were computed to identify gene expression that predicts disease recurrence after curative resection (HCCs n=48). Claudin-10 ranks high in prognosis prediction and is membrane bound protein with potential therapeutic value.

Claudin-10 encodes a member of the claudin family in which claudins are integral membrane proteins and components of tight junction strands. The claudin-10 level by cDNA microarray was significantly associated with recurrence (hazard ratio (HR) 1.7, 95% confidence interval [CI] 1.1-2.6, P=0.014). To verify the technical concern on cDNA microarray reproducibility, quantitative RT-PCR was performed on the same HCC sample set. Results derived from the two research methods demonstrated a high concordance (Pearson correlation coefficient, r=0.602, P<0.001).

To provide an independent test of the association between claudin-10 expression and disease recurrence, a second set of primary HCCs was used (n=53). Quantitative RT-PCR was employed to measure the abundance of the claudin-10 transcript. The claudin-10 level was treated as a continuous variable, and Cox regression analysis was used to examine the relationship of the transcript level with disease recurrence of the patients after curative HCC surgery. Results indicated that the transcript level of claudin-10 was significantly associated with recurrence (HR 1.2, 95% CI 1.0-1.4, P=0.011). Thus, the two sample sets examined by different techniques both indicated that a higher expression level of claudin-10 in HCC was associated with disease recurrence after curative surgery. Prognosis by Claudin-10 Expression and Clinico-pathological Features. All the 101 patients in the two sample sets were included into the disease recurrence analyses. The claudin-10 expression data was based on quantitative RT-PCR, and was modeled as continuous variable in the analyses. For clinico-pathological parameters, patients were dichotomized accordingly (Table 3).

TABLE 3

Cox regression analyses for disease-free survival on gene expression and clinico-pathological parameters

| Variables[a] | n | Univariable Analysis Hazard ratio (95% CI) | P | Multivariable Analysis Adjusted Hazard ratio (95% | P |
|---|---|---|---|---|---|
| pTNM stage | | | | | |
| Stage I and II | 43 | 1 | | 1 | |
| Stage III and | 58 | 3.0 (1.7-5.4) | <0.001 | 2.6 (1.4- | 0.002 |
| Tumor size | | | | | |
| ≦5 cm | 39 | 1 | | 1 | |
| >5 cm | 62 | 2.2 (1.2-3.8) | 0.006 | 2.7 (1.5- | 0.001 |
| Venous | | | | | |
| Absence | 48 | 1 | | | |
| Presence | 53 | 2.6 (1.5-4.5) | 0.001 | — | — |
| Tumor nodule | | | | | |
| Single | 77 | 1 | | | |
| Multiple | 24 | 1.9 (1.1-3.3) | 0.025 | — | — |
| Microsatellite | | | | | |
| Absence | 52 | 1 | | | |
| Presence | 49 | 1.7 (1.0-2.9) | 0.037 | — | — |

TABLE 3-continued

Cox regression analyses for disease-free survival on gene expression and clinico-pathological parameters

| Variables[a] | n | Univariable Analysis | | Multivariable Analysis | |
|---|---|---|---|---|---|
| | | Hazard ratio (95% CI) | P | Adjusted Hazard ratio (95% | P |
| Serum AFP level | | | | | |
| ≦20 ng/ml | 34 | 1 | | 1 | |
| >20 ng/ml | 67 | 1.6 (0.9-2.8) | 0.112 | 2.2 (1.2- | 0.010 |
| Claudin-10[b] | 101 | 1.2 (1.1-1.3) | 0.002 | 1.2 (1.1-1.3) | <0.001 |

[a]Insignificant variables with P > 0.05 were not listed in the table including gender (male versus female), age (≦60 versus >60 years old), hepatitis B virus association (absence versus presence of serum hepatitis B surface antigen), chronic liver disease (normal and hepatitis versus cirrhosis of the liver remnant), tumor encapsulation (absence versus presence of tumor capsule), and Edmondson-Steiner histological grade (Grade 1 and 2 versus 3 and 4).
[b]The claudin-10 expression level (relative fold change in log 2 base) examined by quantitative RT-PCR was modeled as continuous variable in the analyses.

By univariable Cox regression analysis, claudin-10 expression (HR 1.2, 95% CI 1.1-1.3, P=0.002), late pTNM stages (HR 3.0, 95% CI 1.7-5.4, P<0.001), venous invasion (HR 2.6, 95% CI 1.5-4.5, P<0.001), large tumor size (HR 2.2, 95% CI 1.2-3.8, P=0.006), multiple tumor nodules (HR 1.9, 95% CI 1.1-3.3, P=0.025), and microsatellite nodules (HR 1.7, 95% CI 1.0-2.9, P=0.037) were all significantly associated with disease recurrence. Gender, age, HBV association, serum AFP level, cirrhosis in the remnant liver, tumor encapsulation, and Edmondson-Steiner histological grade were not significantly associated with recurrence.

By multivariable Cox regression analysis, claudin-10 expression (HR 1.2, 95% CI 1.1.1-1.3, P<0.001), late pTNM stage (HR 2.6, 95% CI 1.4-4.7, P=0.002), large tumor size (HR 2.7, 95% CI 1.5-4.9, P=0.001) and high serum AFP level (HR 2.2, 95% CI 1.2-4.0, P=0.010) were independent prognostic factors for disease recurrence. The other clinico-pathological features did not add independent prognostic information.

The Kaplan-Meier plot was used to further examine the prediction power by using the claudin-10 expression level alone or together with the pTNM stage system because these two factors were independent prognostic indicators by Cox regression analysis. By Youden index, the optimal cut-off value of claudin-10 expression was 1.23 (relative fold change in log 2 base) to segregate patients into low or high claudin-10 expression group. Using this cut off value, there were 60 patients in the low claudin-10 expression group (range 0-1.15), and 41 patients in the high claudin-10 expression group (range 1.30-11.21). By using the claudin-10 factor alone to segregate the patients, the cumulative 3-year disease-free survivals for patients with low and high claudin-10 levels were 53.3% (32/60) and 24.4% (10/41), respectively (log-rank test, P<0.001) (FIG. 1). The analysis was repeated based on the claudin-10 level and pTNM stages of the patients. The cumulative 3-year disease-free survival was 75% (21/28) for early stage (Stages I and II) patients with low claudin-10 level, 40.0% (6/15) for early stage patients with high claudin-10, 34.4% (11/32) for late stage (Stages III and IVa) patients with low claudin-10, and 15.4% (4/26) for late stage patients with high claudin-10 (log-rank test, P<0.001).

Decreased Claudin-10 Expression was Associated with Older Patients, Presence of Tumor Capsule and Non-cirrhotic Liver.

To better understand the significance of claudin-10 expression, the association of claudin-10 expression level with the clinico-pathological parameters of the HCC patients was analyzed. The down-regulation of claudin-10 expression in tumor was significantly associated with older patients (r=−0.223, P=0.025), presence of tumor capsule (P=0.011), and non-cirrhotic liver remnant (r=0.257, P=0.009). The claudin-10 expression level in tumor was not significantly associated with the pTNM stages, venous infiltration, tumor size, multiple tumor nodules, microsatellite nodules, gender, HBV association, serum AFP level, or Edmondson-Steiner histological grade.

Discussion:

In this study, the claudin-10 expression level and its prognostic value as a novel molecular marker for HBV-related HCC was presented. The claudin-10 gene was annotated by the Ensembl automatic analysis pipeline. The claudin-10 gene locates at chromosome 13g31-q34 spanning 25.51 Kb with 5 exons, and the predicted protein contains four potential transmembrane domains. This gene encodes a member of the claudin family in which claudins are integral membrane proteins and components of tight junction strands (refer to ref 16 for review). Tight junction strands serve as a physical barrier to prevent solutes and water from passing freely through the paracellular space between epithelial or endothelial cell sheets. The exact function of claudin-10 is unknown, and its role in cancer development and progression is mysterious. Interestingly, the claudin family members have been shown to facilitate cell invasion and migration (16). Two alternatively spliced transcript variants that encode different isoforms have been reported for the claudin-10 gene (NM_006984 and NM_182848). The two transcripts are identical at the C-terminal and encode 155 amino acids alike. In the databases (GenAtlas, GeneCard, and SwissProt), the claudin-10 mostly refers to claudin-10b or claudin-10 transcript variant 2 (NM_006984, encodes 228 amino acids), and this transcript is also reported to be overexpressed in lung cancer cell lines (17). Nevertheless, claudin-10 variant refers to claudin-10a or claudin-10 transcript variant 1 (NM_182848, encodes 226 amino acids). In this report, the claudin-10 (NM_006984) was characterized for its clinical significance, as it is the predominant isoform observed in various tissue organs (NCBI GenBank) and in liver (unpublished data).

Identification of patients with different risk of disease recurrence will become more important for patient benefit. Here, the microarray data was validated in another independent sample set, and employed quantitative RT-PCR for transcript quantitation in the independent sample set. Both data sets examined by different assay techniques demonstrated that downregulation of claudin-10 expression was associated with prolonged disease-free period after curative surgery. Our results indicated that prognosis for ECC patients can be derived from the gene expression of primary tumors. The use of quantitative RT-PCR to assess the claudin-10 level is particularly feasible for the clinical setting, as the test is sensitive and the assay facilities are commonly available in routine laboratories for practical application. Cox regression multivariate analysis indicated that claudin-10 expression was independent of pTNM stage in predicting prognosis, and gene expression data used together with pTNM stage can have added power to provide more accurate prediction for disease outcome (FIG. 5).

This is the first report on claudin-10 expression associated with disease-free survival in HCC patients after hepatectomy. There have been reports on the expression profiles of HCCs with the microarray approach (14, 20, 25-30), though there have been few reports on the association of gene expressions with HCC patient outcomes. Notably, a recent report by Iizuka and colleagues demonstrated a correlation of gene expression with early post-hepatectomy intrahepatic recurrence within 1 year (31). Claudin-10 did not revealed prognostic significance in that report. The discrepancy may be due to a number of reasons. Firstly, in the study by Iizuka et al., the patients were mostly HCV-related ($^{22}/_{33}$, 66.7%), whereas the majority of our patients were HBV-related ($^{92}/_{101}$, 91.1%). Different HCC etiologies may actually involve different genes and thus recurrence-associated genes in HBV- and HCV-related HCC may be different. Secondly, the fundamental difference in clinical endpoint consideration (only intra-hepatic recurrence within the first year after surgery in the report of Iizuka et al.; both intra- and/or extra-hepatic recurrence within 3 years in our report) may account for the differences, as different genes may be responsible for early recurrence (within the first year) or late recurrence (after the first year). Furthermore, we considered both intra- and extra-hepatic recurrence within 3 years as clinical end-point assessments, because recurrence outside the liver was also important for disease management and the longer follow-up period would have included the majority of recurrence after curative surgery. It would thus be important to evaluate if claudin-10 expression level can predict 3-year disease recurrence in HCV-related HCCs.

The functional annotation of genes provides an insight into the underlying biological mechanism leading to cancer recurrence. The biological function of claudin-10 is unknown. Particularly, claudin family members have been shown to associate with cell invasion and migration (16). Over-expression of claudin-2 transforms a 'tight' tight junction into a 'leaky' tight junction in epithelial cells (32). Over-expression of claudin-11 induces proliferation and enhances migration in an oligodendrocyte cell line (33). Nonetheless, the role of claudins in human cancer is still controversial. Over-expression of claudin-4/-3 has been reported in pancreatic (34,35), colorectal (36), and ovarian (37) cancer. Notably, claudin-4 expression decreases cell invasion and metastatic potential of pancreatic cancer (38). On the other hand, down-regulation of claudin-7/-1 has been reported in head and neck squamous cell carcinomas (39) and breast cancer (40,41). Claudin-10 has not been well characterized (16). Notably, claudin-10 is reported to be highly expressed in lung cancer cell lines (17). Low claudin-10 expression in HCC was associated with the more favorable features including older age of patients, presence of tumor capsule and non-cirrhotic liver remnant. More advanced stages of the HCCs were observed in young patients (9,42). Absence of tumor capsule was an aggressive HCC feature and associated with early recurrence (7,10). Operative mortality was higher in patients with cirrhotic liver, which was related to hepatic function reserve (11,43). The biological role of the decreased claudin-10 level in contribution to favorable HCC prognosis is not clear. Preliminary immunohistochemistry analysis on the cell origin of claudin-10 indicated that in the HCCs with high level of claudin-10 transcript, strong membranous signal and granular cytoplasmic staining was observed in the neoplastic hepatocytes. Nonetheless, further investigation is required to define the role of the prognostic gene claudin-10 in carcinogenesis so as to delineate the exact molecular pathways leading to disease recurrence. These results indicate that claudin-10 expression can predict disease recurrence after curative surgery.

Example III

Synopsis

Among the genes that show prognostic significance and overexpressed in tumor compared with adjacent non-tumorous liver tissues, transcript AA454543 has potential for practical use. The aim of this study was to validate the prognostic significance of transcript AA454543 by alternative research method and in a separate group of HCC patients. The data of transcript AA454543 derived from microarray analysis of the 48 patients having curative partial hepatectomy (Group 1) was verified by quantitative RT-PCR (r=0.618, p<0.001). A separate sample set of HCCs obtained from 53 patients (Group 2) was examined and the association of AA454543 expression level with overall survival was again validated (p=0.027). By Cox regression analysis, transcript AA454543 (hazard ratio 3.0, p=0.017) and pTNM stage (hazard ratio 3.3, p=0.010) were independent prognostic factors for overall survival. The accuracy of prediction for 3-year overall survival for transcript AA454543 (74.2%, p=0.001) and pTNM stage (76.4%, p=0.001) was comparable as measured by the area under the receiver operating characteristic curve. Transcript AA454543 is a potentially useful molecular prognostic marker for overall survival after curative partial hepatectomy for HCC.

Materials and Methods:

Patients and Samples

Forty-eight patients who underwent curative partial hepatectomy during the period March 1999 to April 2000 at Queen Mary Hospital, Hong Kong were selected for the initial study (Group 1). The gene expression profile of these 48 patients had been studied by cDNA microarray [10]. To validate the data obtained from cDNA microarray, in this study, quantitative RT-PCR was performed in HCCs of this group for the AA454543 expression. Another 53 HCC patients (Group 2) operated during the period April 2000 to March 2002 in the same institute with the same inclusion criteria were recruited for further validation study by RT-PCR for transcript AA454543. This independent cohort of patients (Group 2) was used to confirm that the prognostic marker works in general, and not only on the group of patients from whom the data are derived (Group 1) [11]. Patients were included in this study if the pathological examination of the resected specimen showed a clear resection margin. Patients were not selected if the pathological examination showed mixture of other tumor cell types (e.g. cholangiocarcinoma); if they had received chemotherapy before or after resection; if they had undergone liver transplantation instead of partial hepatectomy; if the resection was for recurrence or palliative intent; or if the resection was followed by hospital death. The clinico-pathological data of the 2 groups of patients were listed in Table 4. The age of the patients ranged from 13 to 79, with a median age of 52 years. There were 81 men and 20 women. Serum hepatitis B surface antigen was positive in 92 patients (91.1%). Tumors were staged according to the International Union Against Cancer pathological tumor lymph node metastasis (pTNM) tumor classification 1997 version [12], because the 2002 version did not clearly stratify survival of our patients with advanced stages [13]. The patients were prospectively follow-up for recurrence of HCC. Recurrence was diagnosed based on typical imaging findings in a contrast-enhanced computed tomography scan and an increased serum AFP level. In case of uncertainty, hepatic arteriography and a post-Lipiodol computed tomography scan were performed, and if necessary, fine-needle aspiration cytology was used for confirmation. Up to the date of analysis, 31 out of the total 101 patients succumbed to disease and the median survival period was 12.5 months (range, 4.5-34.1 months). For the remaining 70 patients, the median follow-up period was 33.4 months (range, 14.9-48.8 months).

TABLE 4

Clinico-pathological features of HCCs.

| HCC features | Group 1 n = 48 | Group 2 n = 53 | Total n = 101 |
|---|---|---|---|
| Age | | | |
| Median | 51 | 53 | 52 |
| (Range) | (13-73) | (16-79) | (13-79) |
| Gender | | | |
| Male | 36 | 45 | 81 |
| Female | 12 | 8 | 20 |
| pTNM stage | | | |
| Stage I and II | 22 | 21 | 43 |
| Stage III and | 26 | 32 | 58 |
| Tumor size | | | |
| ≦5 cm | 24 | 15 | 39 |
| >5 cm | 24 | 38 | 62 |
| Venous infiltration | | | |
| Absence | 27 | 21 | 48 |
| Presence | 21 | 32 | 53 |
| Microsatellite | | | |
| Absence | 26 | 25 | 51 |
| Presence | 22 | 28 | 50 |
| Edmondson-Steiner | | | |
| Grade 1 and 2 | 20 | 23 | 43 |
| Grade 3 and 4 | 28 | 30 | 58 |
| Serum AFP level | | | |
| ≦20 ng/ml | 15 | 19 | 34 |
| >20 ng/ml | 33 | 34 | 67 |
| HBsAg | | | |
| Positive | 43 | 49 | 92 |
| Negative | 5 | 4 | 9 |
| Disease mortality | | | |
| Death | 17 | 14 | 31 |
| Alive | 31 | 39 | 70 |

Normal liver specimens from 30 organ donors (8 cadaveric and 22 live donors) were collected in transplant operations performed at the same institution from April 2000 to December 2001 for cDNA microarray study and quantitative RT-PCR assay for transcript AA454543. The organ donors had no underlying liver diseases and were negative for hepatitis B serology. The liver specimens were obtained immediately upon laparotomy to minimize the chance of DNA/RNA alteration as a result of physiological changes or physical manipulation. Informed consents had been obtained for specimen collection. The study protocol was approved by the Ethics Committee of the University of Hong Kong.

Microarray Expression Study

The cDNA microarray slides were printed with about 23,000 cDNA clones including 17,400 genes. Samples, RNA preparations, and hybridization protocols had been established and described in detail previously [10,14]. Data were deposited into the Stanford Microarray Database [15]. The fluorescence signals were normalized by mean-centering genes for each array, and then mean-centering each gene across all arrays. Only well measured genes were included in subsequent analyses, and defined as genes that had a ratio of signal intensity to background noise of more than 1.5 fold and net signal intensity to background of more than 50 unit, for either the Cy5-labeled sample or the Cy3-labeled reference, in at least 50 percent of the tested samples. A total of 1,404 cDNA clones with expression levels different by at least four-fold from the mean in at least two samples were selected for further analyses by Cox regression.

Quantitative RT-PCR for Transcript AA454543

Quantitative RT-PCR was performed as described [16]. Briefly, the first strand cDNA was synthesized from 0.5 µg of total RNA using the High Capacity cDNA Archive kit (Applied Biosystems, Foster City, Calif.) following the manufacturer's instruction. Each 25111 PCR reaction contained 1×PCR buffer II, 5.5 mM $MgCl_2$, 0.2 mM each of dATP, dCTP and dGTP, 0.4 mM dUTP, 0.625 unit AmpliTaq Gold and 5 µl first strand cDNA. Primer and probe reagents for 18s rRNA (Pre-Developed TaqMan Assay Reagents, Applied Biosystems) were used as the endogenous normalization control. Primers and probe for transcript AA454543 were AA454543-F (5'-ACC CAC ACA CAG CGC TCA C-3') (SEQ ID NO:4), AA454543-R (5'-CAA GCC GTA AAA CTT CTG CAT G-3') (SEQ ID NO:5) and AA454543-P (5'-6FAM AGT CAC TCT CAG CGG CCA TCG CCC A-3') (SEQ ID NO:6). Quantification was performed using the ABI Prism 7700 sequence detection system (Applied Biosystems). Transcript quantification was performed in at least triplicates for every sample. The relative amount of transcript AA454543, which had been normalized with control 18s for RNA amount variation and calibrator for plate-to-plate variation, was log-transformed (on a base 2 scale) and presented as the relative fold difference similar to the microarray-based data.

Statistical Methods

Cox regression analyses with gene expression data as continuous variables were computed to examine gene expression that was associated with the overall survival after curative resection. The technical concern of microarray data reproducibility was addressed by using quantitative RT-PCR for validation. Correlation of expression data by microarray and quantitative RT-PCR data were assessed by Spearman correlation test. The association of transcript AA454543 expression and overall survival was validated in Group 2 patients by quantitative RT-PCR.

The overall accuracy of using transcript AA454543 expression level for prognosis prediction was measured by the area under the receiver operating characteristic curve, as there could be limitations of using hazard ratio in gauging the performance of a prognostic marker [17]. The prediction power for 3 years was analyzed. Patients who were alive but with less than 3 years of follow-up were excluded from the prediction study. Thus, 59 patients with 31 of them succumbed to disease were included in this part of analysis. The Youden index (sensitivity+specificity−1) [18] was used to determine the optimal cut-off point of transcript AA454543 expression for the prediction of 3-year overall survival. The Youden index was employed to maximize the sensitivity (true positive fraction) and specificity (1−false positive fraction) of the prediction simultaneously.

The association of gene expression and pTNM stage with patient outcome was examined by univariable and multivariable Cox proportional hazards regression with the forward stepwise selection procedure. The pTNM stage information was categorical data. To ease interpretation, the gene expression data was modeled as categorical variable only in the multivariable Cox regression to comprehend the hazard ratios into a more interpretable scale for direct comparison with pTNM stage. The transcript AA454543 expression data was also modeled as categorical variable in the Kaplan-Meier analyses.

The associations of transcript AA454543 expression level with clinico-pathological features were assessed by the Spearman correlation and Mann-Whitney U test where appropriate. Differences were considered significant when p value is less than 0.05. The statistical analyses were aided by the SPSS version 11.0 software package (SPSS Inc., Chicago, Ill., USA).

Additional Microarray Information

The microarray study was carried out following the MIAME guidelines issued by the Microarray Gene Expression Data Group [19]. The original data are available in the Stanford Microarray Database. Information is also available from the authors on request.

Results:

Transcript AA454543 Expression and Overall Survival

In the cDNA microarray data, the transcript AA454543 ranks high in prognosis prediction and in expression level relative to non-tumors. Higher transcript AA454543 level by cDNA microarray was significantly associated with shorter overall survival (hazard ratio [HR] 1.8, 95% confidence interval [CI] 1.1-3.1, p=0.024) (Table 5). Quantitative RT-PCR was performed on the HCC samples of the Group 1 patients to verify the cDNA microarray data. The two research methods demonstrated a high concordance (Spearman correlation, r=0.618, p<0.001). In Group 2 patients, transcript AA454543 expression level as measured by quantitative RT-PCR showed a significant association with the overall survival (HR 1.4, 95% CI 1.0-2.0, p=0.027) (Table 5).

The two independent sample sets examined by two different techniques both indicated that a higher expression level of transcript AA454543 in HCC was associated with poor overall survival after curative surgery. The two sample sets were then included into Cox regression analyses with transcript AA454543 expression level based on quantitative RT-PCR data. The transcript AA454543 level was significantly associated with overall survival in the combined dataset (HR 1.3, 95% CI 1.1-1.6, p=0.008) (Table 5).

TABLE 5

Cox regression analyses for overall survival on transcript AA454543 expression.[a]

| Patients | n | Hazard ratio | (95% CI) | P |
|---|---|---|---|---|
| Group 1 | 48 | 1.8 | (1.1-3.1) | 0.024 |
| Group 2 | 53 | 1.4 | (1.0-2.0) | 0.027 |
| Group 1 and 2 | 101 | 1.3 | (1.1-1.6) | 0.008 |

[a]The transcript AA454543 expression data was modeled as continuous variable. The expression data was based on the microarray data in the Group 1 patients, and quantitative RT-PCR in the Group 2 patients and the combined groups of patients.

Prognosis by Transcript AA454543 Expression and pTNM Stage

Figure 6:
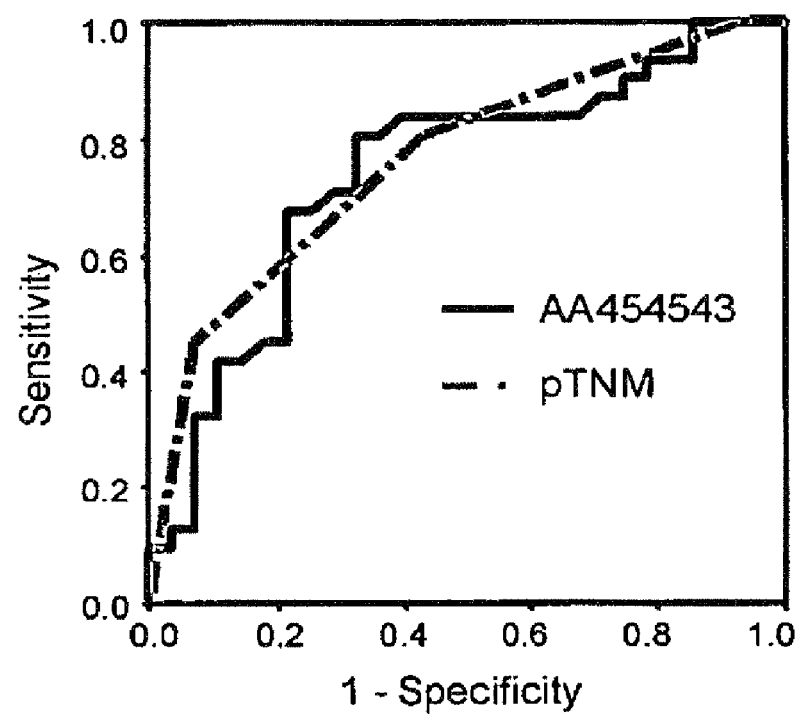
FIG. 6 The accuracy of prediction for overall survival was measured by the area under the receiver operating characteristic curve. The 'sensitivity' (true positive fraction) against '1-specificity' (false positive fraction) was plotted for transcript AA454543 expression level (range 0-11.50) and pTNM stage (I, II, III and IVa), respectively.

All the patients in the two groups were included into the overall survival analyses. The transcript AA454543 expression data was based on quantitative RT-PCR method, and the prediction power for overall survival was compared with pTNM stage. The accuracy of using transcript AA454543 expression for predicting the 3-year overall survival rate was 74.2% (95% CI 61.2-87.2%, p=0.001) measured by the area under the receiver operating characteristic curve (FIG. 6). For comparison, the accuracy of using pTNM stage for survival prediction was 76.4% (95% CI 64.2-88.5%, p=0.001). By Youden index, the optimal cut-off value of transcript AA454543 expression to segregate patients into low or high transcript AA454543 expression group was 7.05 (relative fold change in log 2 base). Using this cut-off value for predicting patient outcome by transcript AA454543 expression, the sensitivity and specificity was 80.6% and 67.9%, respectively. When patients were dichotomized as early stage (stages I and II) or late stage (stages III and IVa) groups, the sensitivity and specificity of prognosis prediction by pTNM stage was 80.6% and 57.1%, respectively.

The Kaplan-Meier plot was used to further examine the prediction power by using the transcript AA454543 expression level alone or together with the pTNM stage system in the total of 101 patients. Using the Youden index as cut-off, there were 43 patients in the low transcript AA454543 expression group (range, 0-7.02), and 58 patients in the high transcript AA454543 expression group (range, 7.08-11.50). By using the transcript AA454543 level alone to segregate the patients, the cumulative 3-year overall survivals for patients with low and high transcript AA454543 levels were 86.0% ($^{37}/_{43}$) and 56.9% ($^{33}/_{58}$), respectively (log-rank test, p=0.001) (FIG. 7). The analysis was repeated based on the transcript AA454543 level and pTNM stages of the patients. The cumulative 3-year overall survivals was 96% ($^{24}/_{25}$) for early stage (Stages I and II) patients with a low transcript AA454543 level, 72.2% ($^{13}/_{18}$) for early stage patients with high transcript AA454543, 72.2% ($^{13}/_{18}$) for late stage (Stages III and IVa) patients with low transcript AA454543, and 50.0% ($^{20}/_{40}$) for late stage patients with high transcript AA454543 (log-rank test, p=0.014).

By Cox regression analysis, transcript AA454543 expression data modeled as continuous variable was significantly associated with the overall survival (Table 5). However, the hazard ratios expressed in their natural scale illustrated only the change in the risk of disease related mortality associated with a change of 1 unit on the expression scale, a change too small to be understood easily. To assist interpretation, the gene expression data was modeled as categorical variable to comprehend the hazard ratios into a more interpretable scale (Table 6). The patients were segregated into low or high transcript AA454543 expression groups similarly as in the Kaplan-Meier analyses, using the Youden index to determine the optimal cut-off value. By univariable Cox regression analysis, transcript AA454543 expression (HR 3.9, 95% CI 1.6-9.6, p=0.003) and late pTNM stage (HR 4.2, 95% CI 1.7-10.3, p=0.002) were significantly associated with the overall survival. By multivariable Cox regression analysis, transcript AA454543 expression (HR 3.0, 95% CI 1.2-7.5, p=0.017) and late pTNM stage (HR 3.3, 95% CI 1.3-8.2, p=0.010) were independent prognostic factors for overall survival.

TABLE 6

Cox regression analyses for overall survival on transcript AA454543 expression and pTNM stage.

| | | Univariable Analysis | | Multivariable Analysis | |
|---|---|---|---|---|---|
| Variables | n | Hazard ratio (95% CI) | P | Adjusted Hazard ratio (95% | P |
| Transcript AA454543[a] | | | | | |
| Low level (0- | 43 | 1 | | 1 | |
| High level (7.08- | 58 | 3.9 (1.6-9.6) | 0.003 | 3.0 (1.2-7.5) | 0.017 |
| pTNM stage[b] | | | | | |
| Early Stage (I | 43 | 1 | | 1 | |
| Late Stage (III and IVa) | 58 | 4.2 (1.7-10.3) | 0.002 | 3.3 (1.3-8.2) | 0.010 |

[a]The transcript AA454543 expression data was modeled as categorical variable. The optimal cut-off value to segregate patients into low or high transcript AA454543 expression group was determined by Youden index, which was 7.05.
[b]The pTNM stage was modeled as categorical variable.

Transcript AA454543 Level in Liver Tissues

Transcript AA454543 expression was higher in the HCC tissues compared to the non-tumor liver tissues adjacent to HCCs in the earlier observation based on the cDNA microarray approach. To validate the observation, we randomly examined 93 (out of a total of 101) liver tissues adjacent to HCCs using real-time quantitative RT-PCR to measure the transcript levels. The results indicated that the HCCs demonstrated a significantly higher transcript AA454543 level (median 7.21, range 0-11.50) compared to that of liver tissues adjacent to HCCs (median 5.54, range 1.26-10.13) ($p<0.001$).

Figure 8:
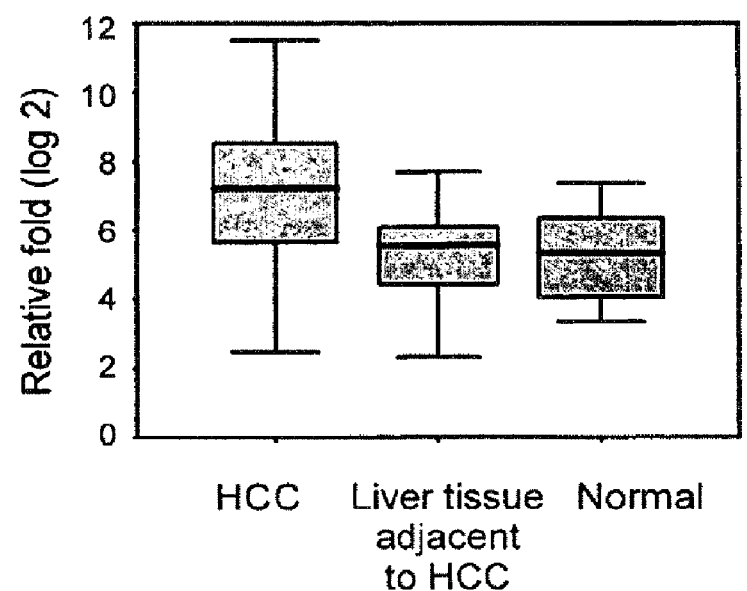
FIG. 8 Transcript AA454543 expression in human liver samples, and transcript level was quantitated by real-time RT-PCR.
Figure 9:
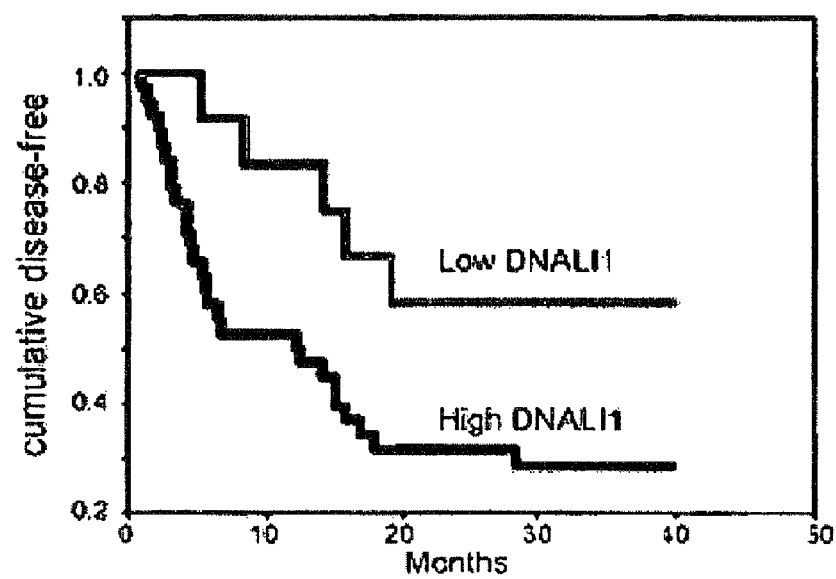
FIG. 9 Validation analysis of DNALI1 gene expression in an independent sample set using quantitative RT-PCR. The prognostic significance of DNALI1 level on disease-free survival was evaluated between patients with high and low tumor DNALI1 levels, stratified using 75 percentile as the cut-off value.
Figure 10:
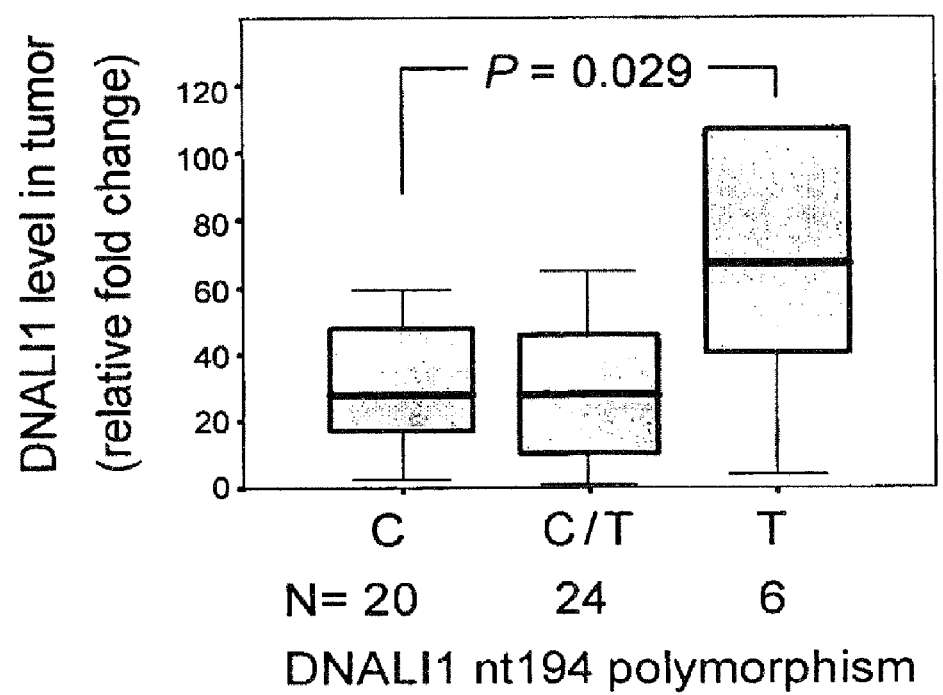
FIG. 10 DNALI1 expression level in tumor was quantitated by real-time RT-PCR. Polymorphism at nucleotide 194 (nt194) was examined by direct sequencing of the blood DNA. Boxplot shows a significantly higher DNALI1 level in patients with T-allele compared to patients with C-allele.

The higher expression level in HCCs than the liver tissues adjacent to HCCs could be interpreted as either transcript AA454543 up-regulation in HCCs or transcript AA454543 down-regulation in liver tissues adjacent to HCCs. To distinguish the two situations, 30 normal liver tissues were examined. In normal livers, the transcript AA454543 transcript was found to express at a low level (median 5.31, range 0-7.36), which was significantly lower than the HCCs ($p<0.001$) but not significantly different from the liver tissues adjacent to HCCs ($p=0.382$) (FIG. 8).

Transcript AA454543 Expression and Clinico-Pathological Features

To better understand the significance of transcript AA454543 expression, we analysed the association of transcript AA454543 expression level with the clinico-pathological parameters of the HCC patients. The up-regulation of transcript AA454543 expression in tumor was significantly associated with late pTNM stage ($r=0.299$, $p=0.002$), venous infiltration ($p<0.001$), microsatellite nodules ($p=0.016$) and high Edmondson-Steiner histological grade ($r=0.276$, $p=0.005$). The transcript AA454543 expression level in tumor was not significantly associated with the tumor size, gender, age, HBsAg positivity, or serum AFP level.

Discussion:

The transcript AA454543 sequence (clone ID IMAGE: 838048; UniGene Cluster Hs.437039; accession BC043195) is 1703 bp mRNA with partial codons and originally cloned from hypothalamus of the human brain. By sequence homologue search with National Center for Biotechnology Information (NCBI) BLAST, the transcript AA454543 shows 95% identities over 1686 bp with AL035705, which is the human DNA sequence from clone RP4-758N20 on chromosome 1p31.3-32.2. Compared with the mouse genome, the transcript AA454543 shows 85% identities over 327 bp with AL929466, which is the DNA sequence on mouse chromosome 4. No known gene in the genomes of human, mouse and model organism shows a high sequence homology with the transcript AA454543 sequence.

Identification of patients with different risk after curative treatment will be more and more important in disease management for patient benefit. The conventional pTNM stage system has been proven informative for identifying patient with different prognosis, and the current study demonstrated that the molecular characteristics of HCC could further add on the prediction power. Thus far, we evaluated the prognostic significance of transcript AA454543 that was chosen based on the analysis of our earlier microarray data. In addition, its transcript level in tumor is significantly higher than the liver tissue adjacent to tumor, which would be important consideration for clinical application and thus was chosen for subsequent validation as molecular prognostic marker. The aim of the study is to consolidate the significance of the prognostic genes, with the assay method quantitative RT-PCR which is a technique readily available in routine laboratories for practical use. In the current study, we reported the prognostic significance of transcript AA454543 whose expression level can predict survival for HCC patients after curative hepatectomy. Transcript AA454543 expression and pTNM stage were independent prognostic factors for overall survival by multivariable Cox regression analyses. Gene expression data together with pTNM stage can help to provide a more accurate overall survival prediction as illustrated in the Kaplan-Meier analyses (FIG. 7). Remarkably, the transcript AA454543 expression (single gene data) and pTNM stage have similar accuracy on prognosis prediction (74.2% and 76.4%, respectively). Our ultimate target is to recruit more genes to increase the accuracy for prognosis prediction.

Expression of alpha-fetoprotein (AFP), cell cycle regulators, genes associated with metabolism, and tumor dedifferentiation status were associated with the molecular subtypes of HCCs [10, 14, 20-25]. However, there have been few HCC reports on the association of gene expressions with patient outcomes. Notably, Iizuka et al. reported the correlation of gene expression profile with early intrahepatic recurrence [26]. There are fundamental differences between the present study and that of the Iizuka et al. report, in that most of the patients in Iizuka's study were HCV-related ($22/33$, 66.7%) whereas the patients in the present study were mostly HBV-related ($92/101$, 91.1% in the present cohort). Different etiological agents may have involved different carcinogenesis pathways, resulting in different molecular composition and behavior. Furthermore, we used the overall survival of 3 years as end-point while Iizuka et al. used intrahepatic recurrence in the first year as the clinical end-point for prognosis prediction. The prognostic genes may be different for prognosis of disease recurrence and overall survival. Nonetheless, we had explored the original data set by Iizuka et al. and transcript AA454543 was not on the probe set list. It would thus be important to evaluate if the transcript AA454543 expression level can predict overall survival in HCV-related HCCs.

The transcript AA454543 has not been well characterized and the biological function is unknown. In the clinical samples, the transcript AA454543 level was significantly higher in HCCs compared to their paralleled liver tissues adjacent to HCCs, and to normal livers. The transcript AA454543 level is informative to differentiate if the liver tissue is neoplastic tissue, in addition to providing prognostic information. Preliminary in situ hybridization analysis on the cell origin of transcript AA454543 indicated that cytoplasmic signal was observed in the neoplastic hepatocytes in HCC tissue. Notably, a higher transcript AA454543 expression level in HCC was associated with poor prognostic features including late pTNM stage, venous infiltration, microsatellite nodules and high Edmondson-Steiner Grade. The association study of the transcript AA454543 level with the clinico-pathological features is exploratory in nature and further experiments are needed to examine their causal relationship, for example, if an increased transcript AA454543 level will result in enhancing the invasive ability of the tumor cells thus resulting in venous infiltration and formation of microsatellite nodules. In the hierarchical clustering analysis, transcript AA454543 was found to cluster closely with the proliferation cluster, tightly with G protein-coupled receptor and zinc finger protein, which play an important role in coordinating cell cycle progression. These genes that co-expressed with transcript AA454543 will help to provide a hint of the transcript AA454543 function.

The present study indicates that the transcript AA454543 expression level can predict overall survival of the patients after curative partial hepatectomy. The current approach demonstrates the power of expression profiles to identify prognostic markers feasible for clinical application. It also opens the prospect for considering unknown genes and not only focus on well-known genes with recognized biological contribution in carcinogenesis. This molecular marker provides prognostic information in general (two independent cohort of patients) and the prediction is independent of assay method (microarray or quantitative RT-PCR). By quantitative RT-PCR, this gene is feasible for routine laboratory assay. And together with pTNM stage, it could help to improve prognosis prediction and disease management for patient benefit.

Example IV

Synopsis

Dynein, axonemal, light intermediate polypeptide 1 (DNALI1) expression was found to significantly associate with disease recurrence (hazard ratio [HR] 1.7, 95% confidence interval [CI] 1.1-2.6, P=0.014) as shown in our earlier genome-wide expression study by cDNA microarray approach on hepatocellular carcinoma (HCC). This study was performed on an independent sample set (n=50) and employed quantitative RT-PCR to examine the DNALI1 transcript level. The association of higher DNALI1 expression level with early disease recurrence was again confirmed. Our preliminary sequencing study indicated that DNALI1 had a polymorphism at nucleotide 194: (codon 65), which either harbored the C-allele (GCA, alanine) or T-allele (GTA, valine). We then further examined the blood samples of the patients for the nucleotide 194 polymorphism (n=50, paralleled samples where the HCCs had quantitative RT-PCR data). The tumor DNALI1 transcript level was significantly higher in patients with T-allele compared to patients with C-allele (median 67.2 and 27.6, respectively; P=0.029). The investigation on clinical samples confirmed that DNALI1 expression level was associated with early disease recurrence, and the DNALI1 level was higher in patients with the T-allele at nucleotide 194.

References for Example I

1. Pisani, P., Parkin, D. M., Bray, F. & Ferlay, J. "Estimates of the Worldwide Mortality from 25 Cancers in 1990", *Int. J. Cancer* 83, 18-29 (1999).
2. El-Serag, H. B. & Mason, A. C., "Rising Incidence of Hepatocellular Carcinoma in the United States", *N. Engl. J. Med.* 340, 745-750 (1999).
3. Taylor-Robinson, S. D., Foster, G. R., Arora, S., Hargreaves, S. & Thomas, H. C., "Increase in Primary Liver Cancer in the UK, 1979-94", *Lancet* 350:1142-1143 (1997).
4. Okuda, K., Fujimoto, I., Hanai, A. & Urano, Y., "Changing Incidence of Hepatocellular Carcinoma in Japan," *Cancer Res.* 47, 4967-4972 (1987).
5. Tang, Z. Y., "Hepatocellular Carcinoma", *J. Gastroenterol. Hepatol.* 15 Suppl, G1-7 (2000).
6. Ng, I. O., Lai, E. C., Fan, S. T., Ng, M. M. & So, M. K., "Prognostic Significance of Pathologic Features of Hepatocellular Carcinoma. A Multivariate Analysis of 278 Patients", *Cancer* 76, 2443-2448 (1995).
7. Ng, I. O., Poon, R. T., Shek, T. W. & Fan, S. T., "Clinicopathologic and Prognostic Significance of the Histologic Activity of Noncancerous Liver Tissue in Hepatitis B Virus-Associated Hepatocellular Carcinoma", *Am. J. Clin. Pathol.* 117, 411-418 (2002).
8. Poon, R. T. et al., "Different Risk Factors and Prognosis for Early and Late Intrahepatic Recurrence After Resection of Hepatocellular Carcinoma", *Cancer* 89, 500-507 (2000).
9. Poon, R. T. et al., "Improving Survival Results After Resection of Hepatocellular Carcinoma: A Prospective Study of 377 Patients over 10 Years", *Ann. Surg.* 234, 63-70 (2001).
10. Poon, R. T. et al., "Clinicopathologic Features of Long-Term Survivors and Disease-Free Survivors After Resection of Hepatocellular Carcinoma: A Study of a Prospective Cohort", *J. Clin. Oncol.* 19, 3037-3044 (2001).
11. Vauthey, J. N. et al., "Simplified Staging for Hepatocellular Carcinoma", *J. Clin. Oncol.* 20, 1527-1536 (2002).
12. Villa, E. et al., "Estrogen Receptor Classification for Hepatocellular Carcinoma: Comparison With Clinical Staging Systems", *J. Clin. Oncol.* 21, 441-446 (2003).
13. Yeatman, T. J., "The Future of Cancer Management: Translating the Genome, Transcriptome, and Proteome", *Ann. Surg. Oncol.* 10, 7-14 (2003).
14. Beer, D. G. et al., "Gene-Expression Profiles Predict Survival of Patients with Lung Adenocarcinoma," *Nat. Med.* 8, 816-824 (2002).
15. Dhanasekaran, S. M. et al., "Delineation of Prognostic Biomarkers in Prostate Cancer", *Nature* 412, 822-826 (2001).
16. Garber, M. E. et al., "Diversity of Gene Expression in Adenocarcinoma of the Lung", *Proc. Natl. Acad. Sci. USA* 98, 13784-13789 (2001).
17. Pomeroy, S. L. et al., "Prediction of Central Nervous System Embryonal Tumour Outcome Based on Gene Expression", *Nature* 415, 436-442 (2002).
18. Singh, D. et al., "Gene Expression Correlates of Clinical Prostate Cancer Behavior", *Cancer Cell* 1, 203-209 (2002).
19. Sorlie, T. et al., "Gene Expression Patterns of Breast Carcinomas Distinguish Tumor Subclasses with Clinical Implications", *Proc. Natl. Acad. Sci. USA* 98, 10869-10874 (2001)
20. van de Vijver, M. J. et al., "A Gene-Expression Signature as a Predictor of Survival in Breast Cancer", *N. Engl. J. Med.* 347, 1999-2009 (2002).
21. van't Veer, L. J. et al., "Gene Expression Profiling Predicts Clinical Outcome of Breast Cancer", *Nature* 415, 530-536 (2002).
22. Kawai, H. F., Kaneko, S., Honda, M., Shirota, Y. & Kobayashi, K., "Alpha-Fetoprotein-Producing Hepatoma Cell Lines Share Common Expression Profiles of Genes in Various Categories Demonstrated by cDNA Microarray Analysis", *Hepatology* 33, 676-691 (2001).
23. Lee, J. & Thorgeirsson, S. S., "Functional and Genomic Implications of Global Gene Expression Profiles in Cell Lines from Human Hepatocellular Cancer", *Hepatology* 35, 1134-1143 (2002).
24. Okabe, H. et al., "Genome-Wide Analysis of Gene Expression in Human Hepatocellular Carcinomas Using cDNA Microarray: Identification of Genes Involved in Viral Carcinogenesis and Tumor Progression", *Cancer Res.* 61, 2129-2137 (2001).
25. Shirota, Y., Kaneko, S., Honda, M., Kawai, H. F. & Kobayashi, K., "Identification of Differentially Expressed Genes in Hepatocellular Carcinoma with cDNA Microarrays", *Hepatology* 33, 832-840 (2001).
26. Xu, X. R. et al., "Insight into Hepatocellular Carcinogenesis at Transcriptome Level by Comparing Gene Expression Profiles of Hepatocellular Carcinoma with Those of Corresponding Noncancerous Liver" *Proc. Natl. Acad. Sci. USA* 98, 15089-15094 (2001).
27. Chen, X. et al., "Gene Expression Profiles in Human Liver Cancers", *Mol. Biol. Cell* 13, 1929-1939 (2002).

28. Cheung, S. T. et al., "Identify Metastasis-Associated Genes in Hepatocellular Carcinoma Through Clonality Delineation for Multi-Nodular Tumor", *Cancer Res.* 62, 4711-4721 (2002).
29. Iizuka, N. et al., "Oligonucleotide Microarray for Prediction of Early Intrahepatic Recurrence of Hepatocellular Carcinoma After Curative Resection", *Lancet* 361, 923-929 (2003).
30. Sobin, L. H. & Whitekind, C., "*In TNM Classification of Malignant Tumours*," John Wiley, New York, 5th ed. 1997).
31. Youden, W. J., "Index for Rating Diagnostic Tests", *Cancer* 3, 32-35 (1950).
32. Edmondson, H. A. & Steiner, P. E., "Primary Carcinoma of the Liver: A Study of 100 Cases Among 48,900 Necropsies", *Cancer* 7, 462-503 (1954).
33. Gonzalez-Mariscal, L., Betanzos, A., Nava, P. & Jaramillo, B. E., "Tight Junction Proteins", *Prog. Biophys. Mol. Biol.* 81, 1-44 (2003).
34. Kastury, K. et al., "Complementary Deoxyribonucleic Acid Cloning and Characterization of a Putative Human Axonemal Dynein Light Chain Gene", *J. Clin. Endocrinol. Metab.* 82, 3047-3053 (1997).
35. Schwartz, J. D., Schwartz, M., Mandeli, J. & Sung, M., "Neoadjuvant and Adjuvant Therapy for Resectable Hepatocellular Carcinoma Review of the Randomised Clinical Trials", *Lancet Oncol.* 3, 593-603 (2002).
36. Poon, R. T., Fan, S. T. & Wong, J., "Risk Factors, Prevention, and Management of Postoperative Recurrence After Resection of Hepatocellular Carcinoma", *Ann. Surg.* 232, 10-24 (2000).
37. Muto, Y. et al., "Prevention of Second Primary Tumors by an Acyclic Retinoid, Polyprenoic Acid, in Patients with Hepatocellular Carcinoma", *N. Engl. J. Med.* 334, 1561-1567 (1996).
38. Marill, J., Idres, N., Capron, C. C., Nguyen, E. & Chabot, G. G., "Retinoic Acid Metabolism and Mechanism of Action: A Review" *Curr. Drug Metab.* 4, 1-10 (2003).
39. DeRisi, J. et al., "Use of a cDNA Microarray to Analyse Gene Expression Patterns in Human Cancer", *Nat. Genet.* 14, 457-460 (1996).
40. Perou, C. M. et al., "Molecular Portraits of Human Breast Tumours", *Nature* 406, 747-752 (2000).
41. Sherlock, G. et al., "The Stanford Microarray Database", *Nucleic Acids Res.* 29, 152-155 (2001).
42. Eisen, M. B., Spellman, P. T., Brown, P. O. & Botstein, D., "Cluster Analysis and Display of Genome-Wide Expression Patterns", *Proc. Natl. Acad. Sci. USA* 95, 14863-14868 (1998).
43. Bustin, S. A., "Absolute Quantification of mRNA Using Real-Time Reverse Transcription Polymerase Chain Reaction Assays", *J. Mol. Endocrinol.* 25, 169-193 (2000).
44. SAS Institute Inc., "*In SAS Macro Language: Reference*", First Edition. SAS Institute Inc., 1$^{st}$ ed. 1997).
45. Brazma, A. et al., "Minimum Information About a Microarray Experiment (MIAME)-Toward Standards for Microarray Data", *Nat. Genet.* 29, 365-371 (2001).

References for Example II

1. Pisani, P., Parkin, D. M., Bray, F., and Ferlay, J. Estimates of the worldwide mortality from 25 cancers in 1990. Int. J. Cancer, 83:18-29, 1999.
2. El-Serag, H. B., and Mason, A. C. Rising incidence of hepatocellular carcinoma in the United States. N. Engl. J. Med. 340:745-750, 1999.
3. Taylor-Robinson, S. D., Foster, G. R., Arora, S., Hargreaves, S., and Thomas, H. C. Increase in primary liver cancer in the UK, 1979-94. Lancet, 350:1142-1143, 1997.
4. Okuda, K., Fujimoto, I., Hanai, A., and Urano, Y. Changing incidence of hepatocellular carcinoma in Japan. Cancer Res., 47:4967-4972, 1987.
5. Tang Z Y. Hepatocellular carcinoma. J. Gastroenterol. Hepatol., 15 Suppl:G1-G7, 2000.
6. Ng, I. O., Lai, E. C., Fan, S. T., Ng, N. M., and So, M. K. Prognostic significance of pathologic features of hepatocellular carcinoma. A multivariate analysis of 278 patients. Cancer, 76:2443-2448, 1995.
7. Poon, R. T., Fan, S. T., Ng, I. O., Lo, C. M., Liu, C. L., and Wong, J. Different risk factors and prognosis for early and late intrahepatic recurrence after resection of hepatocellular carcinoma. Cancer, 89:500-507, 2000.
8. Poon, R. T., Ng, I. O., Fan, S. T., et al. Clinicopathologic features of long-term survivors and disease-free survivors after resection of hepatocellular carcinoma: a study of a prospective cohort. J. Clin. Oncol., 19:3037-3044, 2001.
9. Ng, I. O., Ng, M. M., Lai, E. C., and Fan, S. T. Pathologic features and patient survival in hepatocellular carcinoma in relation to age. J. Surg. Oncol., 61:134-137, 1996.
10. Ng, I. O., Lai, E. C., Ng, M. M., and Fan, S. T. Tumor encapsulation in hepatocellular carcinoma. A pathologic study of 189 cases. Cancer, 70:45-49, 1992.
11. Fan, S. T. Methods and related drawbacks in the estimation of surgical risks in cirrhotic patients undergoing hepatectomy. Hepatogastroenterology, 49:17-20, 2002.
12. Vauthey, J. N., Lauwers, G. Y., Esnaola, N. F., et al. Simplified staging for hepatocellular carcinoma. J. Clin. Oncol., 20:1527-1536, 2002.
13. Villa, E., Colantoni, A., Camma, C., et al. Estrogen receptor classification for hepatocellular carcinoma: comparison with clinical staging systems. J. Clin. Oncol., 21:441-446, 2003.
14. Chen, X., Cheung, S. T., So, S., et al. Gene expression patterns in human liver cancers. Mol. Biol. Cell, 13:1929-1939, 2002.
15. Simon R, Radmacher M D, Dobbin K, et al. Pitfalls in the use of DNA microarray data for diagnostic and prognostic classification. J Natl Cancer Inst 2003; 95:14-18.
16. Gonzalez-Mariscal, L., Betanzos, A., Nava, P., and Jaramillo, B. E. Tight junction proteins. Prog. Biophys. Mol. Biol., 81:1-44, 2003.
17. Sugita M, Geraci M, Gao B, Powell R L, Hirsch F R, Johnson G, Lapadat R, Gabrielson E, Bremnes R, Bunn P A, Franklin W A. Combined use of oligonucleotide and tissue microarrays identifies cancer/testis antigens as biomarkers in lung carcinoma. Cancer Res 2002; 62(14): 3971-3979.
18. Sobin, L. H., and Whitekind, C. TNM classification of malignant tumours. 5th ed. New York, John Wiley, 1997.
19. Poon, R. T., and Fan, S. T. Evaluation of the new AJCC/UICC staging system for hepatocellular carcinoma after hepatic resection in Chinese patients. Surg. Oncol. Clin. N. Am., 12:35-50, 2003.
20. Cheung, S. T., Chen, X., Guan, X. Y., et al. Identify metastasis-associated genes in hepatocellular carcinoma through clonality delineation for multi-nodular tumor. Cancer Res., 62:4711-4721, 2002.
21. Sherlock, G., Hernandez-Boussard, T., Kasarskis, A., et al. The Stanford Microarray Database. Nucleic Acids Res., 29:152-155, 2001.
22. Bustin, S. A. Absolute quantification of mRNA using real-time reverse transcription polymerase chain reaction assays. J. Mol. Endocrinol., 25:169-193, 2000.

23. Youden, W. J. Index for rating diagnostic tests. Cancer, 3:32-35, 1950.
24. Brazma, A., Hingamp, P., Quackenbush, J., et al. Minimum information about a microarray experiment (MIAME)-toward standards for microarray data. Nat. Genet., 29:365-371, 2001.
25. Kawai, H. F., Kaneko, S., Honda, M., Shirota, Y., and Kobayashi, K. Alpha-fetoprotein-producing hepatoma cell lines share common expression profiles of genes in various categories demonstrated by cDNA microarray analysis. Hepatology, 33:676-691, 2001.
26. Lee, J., and Thorgeirsson, S. S. Functional and genomic implications of global gene expression profiles in cell lines from human hepatocellular cancer. Hepatology, 35:1134-1143, 2002.
27. Neo S Y, Leow C K, Vega V B, Long P M, Islam A F, Lai P B, Liu E T, et al. Identification of discriminators of hepatoma by gene expression profiling using a minimal dataset approach. Hepatology 2004; 39:944-953.
28. Okabe, H., Satoh, S., Kato, T., et al. Genome-wide analysis of gene expression in human hepatocellular carcinomas using cDNA microarray: identification of genes involved in viral carcinogenesis and tumor progression. Cancer Res., 61:2129-2137, 2001.
29. Shirota, Y., Kaneko, S., Honda, M., Kawai, H. F., and Kobayashi, K. Identification of differentially expressed genes in hepatocellular carcinoma with cDNA microarrays. Hepatology, 33:832-840, 2001.
30. xu, X. R., Huang, J., Xu, Z. G., et al. Insight into hepatocellular carcinogenesis at transcriptome level by comparing gene expression profiles of hepatocellular carcinoma with those of corresponding noncancerous liver. Proc. Natl. Acad. Sci. U.S.A., 98:15089-15094, 2001.
31. Iizuka, N., Oka, M., Yamada-Okabe, H., et al. Oligonucleotide microarray for prediction of early intrahepatic recurrence of hepatocellular carcinoma after curative resection. Lancet, 361:923-929, 2003.
32. Amasheh, S., Meiri, N., Gitter, A. H., et al. Claudin-2 expression induces cation-selective channels in tight junctions of epithelial cells. J. Cell Sci., 115:4969-4976, 2003.
33. Tiwari-Woodruff, S. K., Buznikov, A. G., Vu, T. Q., et al. OSP/claudin-11 forms a complex with a novel member of the tetraspanin superfamily and beta1 integrin and regulates proliferation and migration of oligodendrocytes. J. Cell Biol., 153:295-305, 2001.
34. Nichols, L. S., Ashfaq, R., and Iacobuzio-Donahue, C. A. Claudin 4 protein expression in primary and metastatic pancreatic cancer: support for use as a therapeutic target. Am. J. Clin. Pathol., 121:226-230, 2004.
35. Michl, P., Buchholz, M., Rolke, M., et al. Claudin-4: a new target for pancreatic cancer treatment using *Clostridium perfringens* enterotoxin. Gastroenterology, 121:678-684, 2001.
36. Miwa, N., Furuse, M., Tsukita, S., Niikawa, N., Nakamura, Y., Furukawa, Y. Involvement of claudin-1 in the beta-catenin/Tcf signaling pathway and its frequent upregulation in human colorectal cancers. Oncol. Res. 12:469-476, 2000.
37. Rangel, L. B., Agarwal, R., D'Souza, T., et al. Tight junction proteins claudin-3 and claudin-4 are frequently overexpressed in ovarian cancer but not in ovarian cystadenomas. Clin. Cancer Res., 9:2567-2575, 2003.
38. Michl, P., Barth, C., Buchholz, M., et al. Claudin-4 expression decreases invasiveness and metastatic potential of pancreatic cancer. Cancer Res., 63:6265-6271, 2003.
39. Al Moustafa, A. E., Alaoui-Jamali, M. A., Batist, G., et al. Identification of genes associated with head and neck carcinogenesis by cDNA microarray comparison between matched primary normal epithelial and squamous carcinoma cells. Oncogene, 21:2634-2640, 2002.
40. Kominsky, S. L., Argani, P., Korz, D., et al. Loss of the tight junction protein claudin-7 correlates with histological grade in both ductal carcinoma in situ and invasive ductal carcinoma of the breast. Oncogene, 22:2021-2033, 2003.
41. Kramer, F., White, K., Kubbies, M., Swisshelm, K., and Weber, B. H. Genomic organization of claudin-1 and its assessment in hereditary and sporadic breast cancer. Hum. Genet., 107:249-256, 2000.
42. Furuta, T., Kanematsu, T., Matsumata, T., et al. Clinicopathologic features of hepatocellular carcinoma in young patients. Cancer 66: 2395-2398, 1990.
43. Vauthey, J. N., Klimstra, D., Franceschi, D., et al. Factors affecting long-term outcome after hepatic resection for hepatocellular carcinoma. Am. J. Surg., 169:28-34, 1995.

References for Example III

1. Pisani P, Parkin D M, Bray F, and Ferlay J (1999). Estimates of the worldwide mortality from 25 cancers in 1990. *Int J Cancer* 83, 18-29.
2. Bruix J, Boix L, Sala M, and Llovet J M. Focus on hepatocellular carcinoma (2004). *Cancer Cell* 5, 215-219.
3. Fan S T, Lo C M, Liu C L, Lam C M, Yuen W K, Yeung C, and Wong J (1999). Hepatectomy for hepatocellular carcinoma: toward zero hospital deaths. *Ann Surg* 229, 322-330.
4. Fong Y, Sun R L, Jarnagin W, and Blumgart L H (1999). An analysis of 412 cases of hepatocellular carcinoma at a Western center. *Ann Surg* 229, 790-799.
5. Neuhaus P, Jonas S, and Bechstein WO (2000). Hepatoma of the liver—resection or transplantation? *Langenbecks Arch Surg* 385, 171-178.
6. Poon R T, Fan S T, Lo C M, Ng I O, Liu C L, Lam C M, and Wong J (2001). Improving survival results after resection of hepatocellular carcinoma: a prospective study of 377 patients over 10 years. *Ann Surg* 234, 63-70.
7. Nagasue N, Kohno H, Chang Y C, Taniura H, Yamanoi A, Uchida M, Kimoto T, Takemoto Y, Nakamura T, and Yukaya R (1993). Liver resection for hepatocellular carcinoma. Results of 229 consecutive patients during 11 years. *Ann Surg* 217, 375-384.
8. Lise M, Bacchetti S, Da Pian P, Nitti D, Pilati P L, and Pigato P (1998). Prognostic factors affecting long term outcome after liver resection for hepatocellular carcinoma: results in a series of 100 Italian patients. *Cancer* 82, 1028-1036.
9. Vauthey J N, Klimstra D, Franceschi D, Tao Y, Fortner J, Blumgart L, and Brennan M (1995). Factors affecting long-term outcome after hepatic resection for hepatocellular carcinoma. *Am J Surg* 169, 28-35.
10. Chen X, Cheung S T, So S, Fan S T, Barry C, Higgins J, Lai K M, Ji J, Dudoit S, Ng I O, et al. (2002). Gene expression patterns in human liver cancers. *Mol Biol Cell* 13, 1929-1939.
11. Simon R, Radmacher M D, Dobbin K, and McShane L M (2003). Pitfalls in the use of DNA microarray data for diagnostic and prognostic classification. *J Natl Cancer Inst* 95, 14-18.
12. Sobin L H, and Whitekind C (1997). TNM classification of malignant tumours. 5th ed. John Wiley, New York, USA.
13. Poon R T, and Fan S T (2003). Evaluation of the new AJCC/UICC staging system for hepatocellular carcinoma after hepatic resection in Chinese patients. *Surg Oncol Clin N Am* 12, 35-50.

14. Cheung S T, Chen X, Guan X Y, Wong S Y, Tai L S, Ng I O, So S, and Fan S T (2002). Identify metastasis-associated genes in hepatocellular carcinoma through clonality delineation for multi-nodular tumor. *Cancer Res* 62, 4711-4721.
15. Sherlock G, Hernandez-Boussard T, Kasarskis A, Binkley G, Matese J C, Dwight S S, Kaloper M, Weng S, Jin H, Ball C A, et al. (2001). The Stanford Microarray Database. *Nucleic Acids Res* 29, 152-155.
16. Bustin S A (2000). Absolute quantification of mRNA using real-time reverse transcription polymerase chain reaction assays. *J Mol Endocrinol* 25, 169-193.
17. Pepe M S, Janes H, Longton G, Leisenring W, and Newcomb P (2004). Limitations of the odds ratio in gauging the performance of a diagnostic, prognostic, or screening marker. *Am J Epidemiol* 159, 882-890.
18. Youden W J (1950). Index for rating diagnostic tests. *Cancer* 3, 32-35.
19. Brazma A, Hingamp P, Quackenbush J, Sherlock G, Spellman P, Stoeckert C, Aach J, Ansorge W, Ball C A, Causton H C, et al. (2001). Minimum information about a microarray experiment (MIAME)-toward standards for microarray data. *Nat Genet.* 29, 365-371.
20. Kawai H F, Kaneko S, Honda M, Shirota Y, and Kobayashi K (2001). Alpha-fetoprotein-producing hepatoma cell lines share common expression profiles of genes in various categories demonstrated by cDNA microarray analysis. *Hepatology* 33, 676-691.
21. Lee J, and Thorgeirsson SS (2002). Functional and genomic implications of global gene expression profiles in cell lines from human hepatocellular cancer. *Hepatology* 35, 1134-1143.
22. Okabe H, Satoh S, Kato T, Kitahara O, Yanagawa R, Yamaoka Y, Tsunoda T, Furukawa Y, and Nakamura Y (2001). Genome-wide analysis of gene expression in human hepatocellular carcinomas using cDNA microarray: identification of genes involved in viral carcinogenesis and tumor progression. *Cancer Res* 61, 2129-2137.
23. Shirota Y, Kaneko S, Honda M, Kawai H F, and Kobayashi K (2001). Identification of differentially expressed genes in hepatocellular carcinoma with cDNA microarrays. *Hepatology* 33, 832-840.
24. Xu X R, Huang J, Xu Z G, Qian B Z, Zhu Z D, Yan Q, Cai T, Zhang X, Xiao H S, Qu J, et al. (2001). Insight into hepatocellular carcinogenesis at transcriptome level by comparing gene expression profiles of hepatocellular carcinoma with those of corresponding noncancerous liver. *Proc Natl Acad Sci USA* 98, 15089-15094.
25. Neo S Y, Leow C K, Vega V B, Long P M, Islam A F, Lai P B, Liu E T, and Ren E C (2004). Identification of discriminators of hepatoma by gene expression profiling using a minimal dataset approach. *Hepatology* 39, 944-953.
26. Iizuka N, Oka M, Yamada-Okabe H, Nishida M, Maeda Y, Mori N, Takao T, Tamesa T, Tangoku A, Tabuchi H, et al. (2003). Oligonucleotide microarray for prediction of early intrahepatic recurrence of hepatocellular carcinoma after curative resection. *Lancet* 361, 923-929.
27. Collins F S, Green E D, Guttmacher A E, Guyer M S; and US National Human Genome Research (2003). A vision for the future of genomics research. *Nature* 422, 835-847.
28. Mattick J S (2003). The human genome and the future of medicine. *Med J Aust* 179, 212-216.
29. Ayoubi P, Jin X, Leite S, Liu X, Martajaja J, Abduraham A, Wan Q, Yan W, Misawa E, Prade R A (2002) PipeOnline 2.0: automated EST processing and functional data sorting. *Nucleic Acids Res* 30, 4761-4769.

What is claimed is:

1. A method for determining the prognosis of a subject afflicted with hepatocellular carcinoma (HCC), comprising:
    (a) obtaining a tumor sample from the subject;
    (b) determining a level of AA454543 (SEQ ID NO: 12) nucleic acid transcript in the tumor sample;
    (c) comparing the level of AA454543 (SEQ ID NO: 12) nucleic acid transcript from step (b) with a reference level of AA454543 (SEQ ID NO: 12) nucleic acid transcript determined by Youden Index, mean or median value whereby a higher level of AA454543 (SEQ ID NO: 12) nucleic acid transcript in step (b) indicates a poor prognosis.

* * * * *

UNITED STATES PATENT AND TRADEMARK OFFICE
CERTIFICATE OF CORRECTION

PATENT NO. : 8,076,077 B2
APPLICATION NO. : 12/255092
DATED : December 13, 2011
INVENTOR(S) : Siu Tim Cheung and Sheung Tat Fan It is certified that error appears in the above-identified patent and that said Letters Patent is hereby corrected as shown below:

Column 2,
Line 1, "NDRG1 (AA486-403)" should read --NDRG1 (AA486403)--.
Line 7, "EST4 (63706)" should read --EST4 (N63706)--.
Line 22, "NDRG1 (AA486-403)" should read --NDRG1 (AA486403)--.
Line 24, "GFRA1 (AA5±2935)" should read --GFRA1 (AA512935)--.

Column 3,
Line 8, "sample, E whereby" should read --sample, whereby --.

Column 5,
Line 29, "NDRG1 (AA486-403)" should read --NDRG1 (AA486403)--.
Line 54, "NDRG1 (AA486-403)" should read --NDRG1 (AA486403)--.
Lines 64-65, "NDRG1 (AA486-403)" should read --NDRG1 (AA486403)--.

Column 6,
Lines 2-3, "(SEQ TD NO:15)" should read --(SEQ ID NO:15)--.
Line 58, "genes the tumor" should read --genes in the tumor--.

Column 8,
Line 56, "scored 0 point) The" should read --scored 0 point). The--.

Column 9,
Line 65, "column" should read --columns--.

Column 12,
Line 39, "(95% CI 2.4 - 14.0," should read --(95% CI 2.1 - 14.0,--.
Line 51, "did not differed" should read --did not differ--.

Signed and Sealed this
Twentieth Day of March, 2012

David J. Kappos
*Director of the United States Patent and Trademark Office*

CERTIFICATE OF CORRECTION (continued)
U.S. Pat. No. 8,076,077 B2

Column 13,
Line 17, "may also due to" should read --may also be due to--.

Column 18,
Line 15, "chromosome 13g31-q34" should read --chromosome 13q31-q34--.
Line 49, "ECC patients" should read --HCC patients--.

Column 22,
Line 8, "Each 25111 PCR" should read --Each 25µl PCR--.

Column 29,
Line 10, "1997)." should read --(1997).--.
Line 55, "1997)." should read --(1997).--.

Column 30,
Line 9, "Ng, N.M., and" should read --Ng, M.M., and--.

Column 31,
Line 29, "30. xu, X.R.," should read --30. Xu, X.R.,--.

Column 32,
Line 42, "Yukaya R (1993)." should read --Yukaya H (1993).--.

SEQUENCE LISTING

<160> NUMBER OF SEQ ID NOS: 32

<210> SEQ ID NO 1
<211> LENGTH: 19
<212> TYPE: DNA
<213> ORGANISM: Artificial Sequence
<220> FEATURE:
<223> OTHER INFORMATION: PCR primer

<400> SEQUENCE: 1
ctgtggaagg cgtgcgtta                                                    19

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
caaagaagcc caggctgaca                                                   20

<210> SEQ ID NO 3
<211> LENGTH: 15
<212> TYPE: DNA
<213> ORGANISM: Artificial Sequence
<220> FEATURE:
<223> OTHER INFORMATION: PCR primer

<400> SEQUENCE: 3
cctccatgct ggcgc                                                        15

<210> SEQ ID NO 4
<211> LENGTH: 19
<212> TYPE: DNA
<213> ORGANISM: Artificial Sequence
<220> FEATURE:
<223> OTHER INFORMATION: PCR primer

<400> SEQUENCE: 4
acccacacac agcgctcac                                                    19

<210> SEQ ID NO 5
<211> LENGTH: 22
<212> TYPE: DNA
<213> ORGANISM: Artificial sequence
<220> FEATURE:
<223> OTHER INFORMATION: PCR primer

<400> SEQUENCE: 5
caagccgtaa aacttctgca tg                                                22

<210> SEQ ID NO 6
<211> LENGTH: 25
<212> TYPE: DNA
<213> ORGANISM: Artificial Sequence
<220> FEATURE:
<223> OTHER INFORMATION: PCR primer

<400> SEQUENCE: 6
agtcactctc agcggccatc gccca                                             25

<210> SEQ ID NO 7
<211> LENGTH: 418
<212> TYPE: DNA
<213> ORGANISM: Homo sapiens

<400> SEQUENCE: 7
tttttttcct ctcatgctct cttcctgcct tcctcactcc tcaatcattt cctttactct        60
ttcattcttt cctctttttt ttttaaatag ctgaatcatt gggtcacctt aaaccttgtg       120
accaaatcca catggtagaa gcaggatgct cttgactcat gttgagtgcc actgaactca       180
ggaagagtgg tcaaagcaat gtttcagaat cttgcagact gtgtagtggg gttttgctaa       240
ttttgtcttc tctgtgctgt gagggagact aggaactcta gacttccctt ttaaatcatc       300
tttgtcgctc acggtaagtt cagtctgggt ttcttacact tcactggttt tggtagaagc       360
tggacatggt gacatatgct tcttcttgat ttgatcccag ggaagtaaga atgggctg         418

<210> SEQ ID NO 8
<211> LENGTH: 392
<212> TYPE: DNA
<213> ORGANISM: Homo sapiens

<400> SEQUENCE: 8
tttttgcaaa gttacaaatt tattggtctg gaaataaata caaatatctc attaagaaac        60
tcctctggaa agacttgtgc acaatagttt cccatccgta ctcagcctct cttgccccga       120
tccccgactt ttctactcaa ggccagggaa ggctccaagg tgatgggcgg caggtaacga       180
gtcattgcct ctcacgccac ctggaaggct ggactacttc ctcctcccaa ctgcggggtc       240
ccagaaatcc tcgggtccca gtggctgact tacaatattc aattcactct gaccaaactt       300
cctatgagaa aatccacggt gagccaaaat gaaaagtaca aggcagtagt acaggaacct       360

```
ggcagccgca ctggccgccc agaaacgtca gt                                    392
```

<210> SEQ ID NO 9
<211> LENGTH: 406
<212> TYPE: DNA
<213> ORGANISM: Homo sapiens
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 9

```
nnannatant attcccagct tttttgtggn ataatgcgca gaaggnaatg aacacattct      60
acctgcaagc ttcttcctgt gcctttggaa tctgctcctg ccagtctgca gggaaccacg     120
gatctgcttt ccgtcacgta ggaggcattc tcgacaccct ctgtacacag catgcgcttt     180
atttggcttc tcttacgcag cgtagtgact ttcagattta ttcaagctgc tgcgtgcgcc     240
aacagtccac tccttcctag tgctgaggcc cccatcacat gagcacaact gtttcttgtg     300
tgtgatgtgt tgttctctgg gctgtgcaaa aagctgattc tgtcatcacc gcatcttgtc     360
tcatcagtag gagtgaatgg gctgggggg  acagtgggca cagtca                   406
```

<210> SEQ ID NO 10
<211> LENGTH: 433
<212> TYPE: DNA
<213> ORGANISM: Homo sapiens
<220> FEATURE:
<221> NAME/KEY: misc_feature
<222> LOCATION: (370)..(370)
<223> OTHER INFORMATION: n is a, c, g, or t

<400> SEQUENCE: 10

```
taatctaatg tcaaatttta ttcaccttt  tttttcttac aatatgctgt cattcaaaat      60
gtacctcaga agcaactcaa ctcatgcata cagtaggcac tctataaatg ttttaataat     120
taggtgtttt ttggaatgac taaaaatcca gatgtaaaat cccaattggg aagtgcataa     180
tcccatcgta gacaaaatat ataacttaca ataaacattt ttataagaat ttgccccaaa     240
gagggaacac ttaaaatttg gaaattaaaa aataaaaatg caaaagcaag atgaaacaaa     300
caatagtaac ctatttagac aatgatccct ggatcggtgg tgcttacaga ccaagggtta     360
cctgcacccn gtggcgtaag accatctgga cattcggttt aagaagagaa ttatatacct     420
aatatcctct taa                                                       433
```

<210> SEQ ID NO 11
<211> LENGTH: 515
<212> TYPE: DNA
<213> ORGANISM: Homo sapiens

<400> SEQUENCE: 11

```
tcttttttaca tgtccatatt gtattttttt aatgcagcta tgatgtttct gttaaagata    60 ataggggtgga cagagcggtt accaccagga ccagcagtgg gctcagacca cagcttggag   120
gagcagccat tgattttgtg gttatgtggc tggaacaccg agaccttctt tttcataatt   180
accattggaa atacagaggt gtgtattgcc cgacacattg gatttcagct tctgtgcctg   240
taaatttgca cacggtggca aaacatgagt gggaatttca ttctcagacc ctgctggccc   300
cagggctctg ttcttaaccc ggaggcagtg gtggtagcgg cagtggtggt ctgtactggg   360
aaggctggct gccacacggt cacatcggag ccattgccaa aggcttgaat tgcattttta   420
agacatgtat tgtccttgaa gaaattcaaa aatttcaagc actcttctag gtcgttccca   480
ctgttgctgc agtcacacca tggggccaca ctgag                              515
```

```
<210> SEQ ID NO 12
<211> LENGTH: 402
<212> TYPE: DNA
<213> ORGANISM: Homo sapiens

<400> SEQUENCE: 12
gacttttaat ttgattttgt gaaaaaagct tataagcaat cagacaggct gcttttctcc    60
tttgtgtttg ttacctatga gtttcatatg gtgcaaacat taattaggaa gaatctgtaa   120
ctatgaaatg ctatgtaatt caggaagaca tcttttccat atggttaatg aaagacaaat   180
ccttcccata tcatttaaca ctcacaaaaa gtatataaca aacaaaactg aaatttgaat   240
cggagtttat ttgaacagaa aagcactgga agtctgttca tttttttttc ttgaaaccaa   300
ttataaaaag tggtcccaat ttcaacaatt aaaaaaaatt tcaataaat acgtaatgaa    360 gtacttcaat gggtcaatgt atcaacctat ggattttttt tt                      402
```

```
<210> SEQ ID NO 13
<211> LENGTH: 406
<212> TYPE: DNA
<213> ORGANISM: Homo sapiens

<400> SEQUENCE: 13
tttgttgagc aaaagtatga attaggagcc gctctgttta ttggatgggc aggagctcac    60
tgtgcataat tggtggtgtc atattttgct tttcaatatc tgacaacaac aaaacaccca   120
gatacacata caacgggggcc acatctgtca tgtcttctcg gacaaagtat catggtggag   180 aagatttaa aacaacaaac ccttcaaaac agtttgataa aatgcttat gtctaaaga    240 gctcgctggc aagctgcctc ttgagtttgt tataaaagcg aactgttcac aaaatgatcc   300
catcaaggcc ctcccataat taacactcaa aactattttt aaaatatgca tttgaaggca   360
tctgttgatt gtatgggtgt aagtgttctt acatagttag ttatat                  406
```

```
<210> SEQ ID NO 14
<211> LENGTH: 424
<212> TYPE: DNA
<213> ORGANISM: Homo sapiens
<220> FEATURE:
<221> NAME/KEY: misc_feature
<222> LOCATION: (12)..(15)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
```

<400> SEQUENCE: 14

```
ggtaactaaa tnnnncatgc aggtctaatg actaataatt ggagtacggc tgctagacaa    60
ctgcatttta gtatttctct tccattctcc tggttttgta gacccagaag attgaatgag   120
tgacataaat ctttagttcg gggcaagcca gggtgggcta gggtggtaag ctggaggact   180
tcatccttca gttaggctgc acaagtaaca ttacctaaaa ggcactaaca tgctcaggtt   240
ccccagaaag aggcgtaagg aagggcctct ccttaggcag agcttccacc tgccatccgt   300
cttggggttc agtgagcttc aagggctcac aatggggaag gcactgtcat tttccccagg   360
aaaagctgtg ttncccctatg gctggaacca caccccttaca cattctcatc tgggggttnt   420
tagg                                                                424
```

<210> SEQ ID NO 15
<211> LENGTH: 462
<212> TYPE: DNA
<213> ORGANISM: Homo sapiens

<400> SEQUENCE: 15

```
ggagctggct ggaatctctc agcctcacct gccagacaac acccctcct tcctcaccct    60
gtctcctgca ttctcctgaa accttcatcc acacaatgcc tcccaacctc actggctact   120
accgctttgt ctcgcagaag aacatggagg actacctgca agccctaaac atcagcttgg   180
ctgtgcggaa gatcgcgctg ctgctgaagc cggacaagga gatcgaacac cagggcaacc   240
acatgacggt gaggacgctc agcaccttcc gaaactacac tgtgcagttt gatgtgggag   300
tggagtttga ggaggacctc aggagcgtgg acggacgaaa atgccagacc atagtaacct   360
gggaggagga gcacctggtg tgtgtgcaga aaggggaagg tcccaaccgg ggcttggaga   420
cactggcttg gaggacaaat gctgtatctg gaactgactg ca                     462
```

<210> SEQ ID NO 16
<211> LENGTH: 346
<212> TYPE: DNA
<213> ORGANISM: Homo sapiens

<400> SEQUENCE: 16

```
tttttttttt ttttttttaa tttttttattt ttatgggctt tggtgaggga ggtaggtggt    60
agtttgtgaa catgtggtgc tgacaccttt aaaggcatat tctccagatc caggtgtaat   120
ttgtccggag aatctcatct gaagtgaatt tccagagaag gagtagaaag aggaaaaaat   180
gacttttttt cagctaaaca tgcctcagat aaagagctgt gtccactctg cctcctggaa   240
tgccgtgctt tcagtacttg caaaccttaa tctctctact tgtgtttttt ctccctaata   300
agtttgtttt aagtatgttt taaatttttt atggtagtca aagttc                  346
```

<210> SEQ ID NO 17
<211> LENGTH: 500
<212> TYPE: DNA
<213> ORGANISM: Homo sapiens
<220> FEATURE:
<221> NAME/KEY: misc_feature
<222> LOCATION: (500)..(500)
<223> OTHER INFORMATION: n is a, c, g, or t

<400> SEQUENCE: 17

```
ctgtctgaat caactgtacg agttaaacag ttttatttcg aaattaacca acataaacaa    60
caacaacaac aacaacattc actacccatt ccctcgttag gttggaaaac cagtctgaaa   120
aaataaatac aatctgtgac catgaaaagg agcaatcact tatttttccc atatgttttg   180
```

```
aacattattt ttaaaaatag attgggaatc tggagggtaa aatgccgggt cccttcccga      240
gcccttagag cccgaacgtt gtcgaatcgg tcaatgtcca ccccgctgct cacctctgtc      300
ccagcagcgc cggggccagc gcgccctccc gccgcgtctg ggagctggcg gggaaaagca      360
ggtccccggg gggtatcgag tgtccaggga tatccacgca gacatccttg tacttgcaaa      420
tacaaagaaa cacacaggac agagatcagg ctcgcgcagg gctcgatctc ctcggggctc      480
agggttggag ggccgtacan                                                 500

<210> SEQ ID NO 18
<211> LENGTH: 420
<212> TYPE: DNA
<213> ORGANISM: Homo sapiens
<220> FEATURE:
<221> NAME/KEY: misc_feature
<222> LOCATION: (60)..(60)
<223> OTHER INFORMATION: n is a, c, g, or t

<400> SEQUENCE: 18
cattaagaaa catttatttg gataagaaag aaggcctgag ggtaagggc ggggctggcn      60 tgcgtctcag tcctgggacg cagcagcccg cacaggttga gaggggcact tcctcttgct     120
taggttggtg aggatctggt cctggttggg ccggtggaga accacaaagc tctctggagg     180
aaggacgggg cctctgttct cttctacctg gcccatcagc agataactga ctccttttctt    240 catgggggg cactgcttgc aaggcacgta aaacttcagg gaggcaccag tgggtggaga      300
aggcaggtcc agtcctccag ttttataagc accaataaga ctgacagtca cggcaaggcc    360
ctcccctggc tcccgaacca tggacttcac tgtcgcagtc accacaaggc tgctggcaca    420

<210> SEQ ID NO 19
<211> LENGTH: 360
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t

<400> SEQUENCE: 19
aaagagtntt actttattat tttaaaaatt ttgtttgaaa gcctttgtac agaataatat     60
aatgtactgc ataaaatatt tgaaatagat gaagtttaca agtttataaa gatgaaacaa    120
tgagatagtg attacattaa gtggttacat taagtctcag gggaaactga attttttaata  180 ggaaaacacc ctatgtacaa tgttactatt taaatgtatt cttctcatc ttaatgctta     240 gtcttgtcac aaacaagagg gtaatcaaat tgtttctagg aattaaatca gagccatcgt    300
gggtgctgna acantatatg gcataccata tattcaaact gtatttatgg aaantcccnt    360

<210> SEQ ID NO 20
```

<211> LENGTH: 325
<212> TYPE: DNA
<213> ORGANISM: Homo sapiens
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t

<400> SEQUENCE: 20

```
ttctccaaca ataaccactg gtccattggt tcactactta ctcaagaaag acatatactg      60
agatggcttg aaatgtttaa tgcatgtgaa cgttattttt accgtgtttt ggaaaaagat     120
cttgatgtta ttgtcttcct ttattttcca caattaagtg catctaactg tgaattgtat     180
atgggaatta cattattcag catatacata tatttacctg ctttgttcat tctctgtatt     240
caaaattaac agatcatgct ggaaaaccac ttcaaacggt tatattntt acattattag      300
gggggnaaat atattattcc gggaa                                           325
```

<210> SEQ ID NO 21
<211> LENGTH: 355
<212> TYPE: DNA
<213> ORGANISM: Homo sapiens
<220> FEATURE:
<221> NAME/KEY: misc_feature
<222> LOCATION: (314)..(314)
<223> OTHER INFORMATION: n is a, c, g, or t

<400> SEQUENCE: 21

```
acaattctcc gcagatttta ttaattataa ctttttttt cagacgtcct gccatcttct       60
cattcagact tttcttagca aaggtagtcc atggcaagta atgaattccc agtaactagg    120
tctgtaacag aagtaaattc tgtttttatg tttataaact caaaaagtaa catgaagtgc    180
aaacaccttt agttccttcc cctcggtaac cttcttttga tgaaccagtg tgcagcaaac    240
caggatgaag ttggatttgg gtgggatcca cacaggtcat tttcaggcaa gatgagactt    300
cccaagttcc atgnatagat tcatattatc agttatttta tgcattcatt tctcc         355
```

<210> SEQ ID NO 22
<211> LENGTH: 469
<212> TYPE: DNA
<213> ORGANISM: Homo sapiens
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t -continued

<400> SEQUENCE: 22

```
tttgaagaac ctgcattatc gtttattgtg atcctaattc ggtccacagt aacaattgaa      60
actgcctcga ctaaatttta agtttctggg gcagcaccac ctgaaggcag cgactgcttt     120
ttaaaagaca gggttctgac attcagagat ttctgtttct ctatccatca tttttgggca     180
tcttgaatca cctgatttag agtcagtgac atcctgactg gattggttct gctctcgctg     240
ggcgggttaa nacccaaga cccacgtcca cagtgcacct gatgttctcc caagcggtcg      300
tcactttccc aaggaggnca ggtaggcata ccagaacaag agctggccag gttggcgaag     360
aagcacccgg aactttcaaa agggacgtaa nttgaatgtt gatgnactgt agtgggcgtc     420
caaanccggc aagtttcatc ctcagcggcc ggccagaaag ccccctna                   469
```

<210> SEQ ID NO 23
<211> LENGTH: 448
<212> TYPE: DNA
<213> ORGANISM: Homo sapiens

<400> SEQUENCE: 23

```
tttttttttt tgagatcaca ggctttattc ctacaaccac agggcttgag ctgcactggg      60
gcaagaaaac agagtttcat ctgagaatgt ctcttatggg ctgggttctg ttcaggggag     120
ggtgggaaca gaggacaagg aagacaagct cctctggccc taggaacaaa acacatttac     180
tccttcaaag aagcagatga tctgaatacc ctctggagac tgaatctgcc catacagccc     240
ctggagccaa tgggagacag tactggcatc tggcacaaaa gggaattcag acccagaaca     300
gaagcagcaa atattttaa aaatagtaaa ttgttcctgg actcacaaat cattgttttt      360
aagggcaagt gcatgcccaa tataagtact ggggcttcct aagagagctg acataggatt     420
acacagctgc ctccctgctt cagtggag                                         448
```

<210> SEQ ID NO 24
<211> LENGTH: 495
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (212)..(212)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:

<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t

<400> SEQUENCE: 24

```
cgtggggttn actgatggtg gctgctgtca nattccaagt ggcttatggg ataggacaac    60
cccccaggca cttcactgta ggacagttag caccaagagc taaggttgtg agataatgca   120
aatctggcct gtcacctctg cagagtacag gttcccatac tntgaggcag cagcagagag   180
ggaaccacca gagaaacagc ntttcagant tntctttcct ttggtntatg gatatgtgtg   240
tgttctagtc tttggtgggc aatggantct gcagctccat gacaatcttg ttaagtagct   300
tatgtgggga agtnttttcag ggtcacaagg gccacccatt ctaaggcttc tcattttaat   360
ttccccaggg nttaaggagg acaggtgggg ggaaagggna aaaaccttng cacctttgct   420
attacttnaa ttngggattc caggaggccc aatccaatgg cattntttac cctactttttc   480
ttgggcccaa atcca                                                    495
```

<210> SEQ ID NO 25
<211> LENGTH: 414
<212> TYPE: DNA
<213> ORGANISM: Homo sapiens

<400> SEQUENCE: 25

```
ttttttttt tttttttttt tttttactg gggagaaatg catgtatttt gtatatgaga    60
aggatgtaga ttttagagaa acagaagcag agtagtttaa tctgaattttt tgtgtccgcc   120
tccagaattc ataggctgaa atctagtcac caaggtgacg ataatagcag ggccgggcct   180
ttgcggggg aagggaatgc aggcagtgcc ctcttgaatg gaactggcgt ccttataaaa    240
gaggtctctg tgagctgtct tgcccttttc caccatgtga ggacacagca agaaggtttt   300
atctatgaaa caagaggtgg gtcctcacca gacacagaac ctgctgacac cttgatctta   360
gccttctaag ccttcagaac catgagaaat agaattctga tgtttgtcag caac          414
```

<210> SEQ ID NO 26
<211> LENGTH: 389
<212> TYPE: DNA
<213> ORGANISM: Homo sapiens
<220> FEATURE:
<221> NAME/KEY: misc_feature
<222> LOCATION: (301)..(301)
<223> OTHER INFORMATION: n is a, c, g, or t
<220> FEATURE:

<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t

<400> SEQUENCE: 26

```
cccaaatatt tttccatttg cagtttgctg aagctgtgga tgcagaaccc atgaatatgg      60
agggccaact gtattttgta ggcagttgaa acattgccc  tggagctcag gagatggctc     120
tggctggaga attcatgcca agggagcctg catttttcgt ccgtccacgc tcctgaggtc     180
ctcctcaaac tccactccca catcaaactg cacagtgtag tttcggaagg tgctgagcgt     240
cctcaccgtc atgtggttgc cctggtgttc gatctccttg tccggttcag aagcagcgga     300
ntcttccgca cagccaagct gatgtctgtn ggggctgcta aggcctgcag gtagtcccca     360
tgtcttctgc gagacaagng gtatagcca                                       389
```

<210> SEQ ID NO 27
<211> LENGTH: 382
<212> TYPE: DNA
<213> ORGANISM: Homo sapiens
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t

<400> SEQUENCE: 27

```
agctctgcta aaaactccag cgcaatttga tgctgatgaa cttcgtgctg ccatgaaggg      60
ccttggaact gatgaagata ctctaattga gattttggca tcaagaacta acaaagaaat     120
cagagacatt aacagggtct acagagagga actgaagaga gatctggcca agacataac      180
ctcagacaca tctggagatt ttcggaacgc tttgctttct cttgctaagg gtgaccgatc     240
tgaggacttt ggngtgaatg aagacttggc tgattcagat gccagggcct tgtatgaagc     300
aggagangg  agaaagggga cagacgtaan cgtgttccaa taccatcctt accaccagaa     360
gctatccaca acttcgcaga gt                                              382
```

<210> SEQ ID NO 28
<211> LENGTH: 282
<212> TYPE: DNA
<213> ORGANISM: Homo sapiens

<400> SEQUENCE: 28

```
tttttttttt ttttttttg  gcaggccaaa accctagttt atttcagcat cagcagtatc      60
ttagccatca aaaaaataaa ctctaccaag ggtgacggaa gtctctacag caaggctaag     120
ggctcgccag acgggaacat caggggtgca tggtgggcac tgccacggca ataagttagg     180
aagcagcagg gctggtgtcg ggtgtgggcc gggcttcatt tctgggcagg catgaggtcg     240
tcgatggcct ggccctgctc cagccgctgt tccatctcga tg                        282
```

<210> SEQ ID NO 29
<211> LENGTH: 254
<212> TYPE: DNA

<213> ORGANISM: Homo sapiens

<400> SEQUENCE: 29

```
cgtatcagtc accatttta atggggaca atgaagacaa gcacacagga ggtagaatat      60
cagagtgggg ctggatcaag ggcaaaaact ggtcattaag tcatctgaca ttaaatcatt    120
tagccactaa gttatttgtc tactctcact ttaaactcac caaagaagat tctcttaaag    180
aaattatgaa aaatgtacaa tttaacattt taaataaata gtgacagaag ttgtttaaaa    240
aaaaaaaaaa aaaa                                                     254
```

<210> SEQ ID NO 30
<211> LENGTH: 391
<212> TYPE: DNA
<213> ORGANISM: Homo sapiens

<400> SEQUENCE: 30

```
gataggaaat tccacataga aattagaaac ctagtcagag gacaagcttc atacagtatg     60
tatgtacagt tggaactgtt caagtatagt ttcagtgtaa aaagtgctac agtaacaaac   120
cacatttaag aaagagttct tagtagagaa acaataagac aaaataccaa acgtagtaca   180
caacaaattt atgtctcagc tacatgatct aaaagttaaa ggtcccagga gccccatcct   240
gaacttggaa agtgtagcct tcagaggtag tttctggtac aacgttttga tcttcctctt   300
cctctacaga gacatacttc tcaattaagc ttaacgaagc cttatacaca gactcatttt   360
catggttttg tagagcttca atttgtctaa g                                 391
```

<210> SEQ ID NO 31
<211> LENGTH: 331
<212> TYPE: DNA
<213> ORGANISM: Homo sapiens
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t

<400> SEQUENCE: 31

```
acttacttca aataatttta tttgagactt actagagaaa taagtagcaa tgtgtaagtt     60
tctcatccta tacatacatg aatgctcttt ctgaagtgta tgatgagaaa agactttaac   120
aattacttac attactacca ggaggaccag gaagaccacg agcaccaggg aagccagcag   180
caccctgtga aatggtaata tatttttgaa tttcaaaagt agaacaaata actatacaac   240
aaacaaaaag tataatgtgt ggtatgatct gcattgnacc tgaaagtcat tnatgggttc   300
gtgtttcccc tttggaattt taccattana a                                 331
```

<210> SEQ ID NO 32
<211> LENGTH: 474
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)

```
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t

<400> SEQUENCE: 32
agngnggnnn gganacacat ttattgagag cacagtgtgt ttttccttcg cagacaaaga      60
aggatcctta tgcgacgaat actggaatcc agcagctaac ctcattaacg tctgcagcct     120
cttccttcga caaggcccga gattagccct gatgcaagga gagcccgtgg acaagggctg     180
cctggagtgc tgttggagaa taaataagac aagtaagaca agcaagancg ggtgggaagg     240
gactgacctg tcaaaccttt tcaacaaaca tttgctgatc acctcctcta tgccagatcc     300
tgcctgaggc cttcttttat ctcatttaat tctcacaaca accctaggaa ggttgctctc     360
atcgacccca tttccccaga aaaggatag ggaagatctt tcagagaggg tgggggcgtg      420
cctttgggtg attcagtagc atgctcattt ccagaagccc acccagggcc tttg           474
```